United States Patent
Long et al.

(10) Patent No.: US 11,992,700 B2
(45) Date of Patent: *May 28, 2024

(54) LIGHT DELIVERY SYSTEM WITH A FIBER OPTIC DISPOSABLE FOR PREVENTING, REDUCING AND/OR ELIMINATING INFECTIONS DURING INSTITUTIONAL OR IN-HOME USE

(71) Applicant: LIGHT LINE MEDICAL, INC., Salt Lake City, UT (US)

(72) Inventors: Curtis D. Long, Salt Lake City, UT (US); Perry Croll, Sandy, UT (US)

(73) Assignee: Light Line Medical, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,868

(22) Filed: Sep. 19, 2022

(65) Prior Publication Data
US 2023/0075669 A1   Mar. 9, 2023

Related U.S. Application Data

(63) Continuation of application No. 17/579,657, filed on Jan. 20, 2022, now Pat. No. 11,497,932, which is a continuation-in-part of application No. 17/000,736, filed on Aug. 24, 2020, now Pat. No. 11,229,728, and a continuation-in-part of application No. 16/747,315,
(Continued)

(51) Int. Cl.
| | |
|---|---|
| *A61N 5/06* | (2006.01) |
| *A61B 90/98* | (2016.01) |
| *A61M 1/16* | (2006.01) |
| *A61M 1/28* | (2006.01) |

(Continued)

(52) U.S. Cl.
CPC ............ *A61N 5/0624* (2013.01); *A61B 90/98* (2016.02); *A61M 1/285* (2013.01); *A61M 39/105* (2013.01); *A61N 5/0601* (2013.01); *A61N 5/067* (2021.08); *A61M 1/168* (2013.01); *A61N 2005/0626* (2013.01);
(Continued)

(58) Field of Classification Search
CPC .... A61N 5/0624; A61N 5/0601; A61N 5/067; A61N 2005/0626; A61N 2005/063; A61N 2005/0659; A61N 2005/0663; A61N 5/06–2005/073; A61B 90/98; A61B 18/20–18/28; A61M 1/285; A61M 39/105; A61M 1/168
See application file for complete search history.

(56) References Cited

U.S. PATENT DOCUMENTS 11,497,932 B2 * 11/2022 Croll ..................... A61M 1/285

* cited by examiner

*Primary Examiner* — Jonathan T Kuo
(74) *Attorney, Agent, or Firm* — Madson IP, P.C.

(57) ABSTRACT

An electromagnetic radiation (EMR) delivery system for delivering EMR at wavelengths, intensities, exposures, and durations to locations inside and/or outside a patient's body in, on, and surrounding a tubular structure such as a tube, catheter, and/or a catheter extension to prevent, reduce, and/or eliminate infectious agents in, on, or surrounding the tubular structure. A smart light engine box generates the therapeutic EMR, controls treatments, and monitors the health of the system. A fiber optic disposable makes at-home use of the EMR delivery system possible. Specific embodiments of the EMR delivery system for use with peritoneal dialysis catheters, dialysis accesses, and hemodialysis accesses are also disclosed.

20 Claims, 21 Drawing Sheets

Related U.S. Application Data filed on Jan. 20, 2020, now Pat. No. 11,241,585, and a continuation-in-part of application No. 16/364,051, filed on Mar. 25, 2019, now Pat. No. 11,229,808, said application No. 17/000,736 is a continuation-in-part of application No. 16/364,051, filed on Mar. 25, 2019, now Pat. No. 11,229,808, which is a continuation-in-part of application No. 15/668,266, filed on Aug. 3, 2017, now Pat. No. 10,307,612, said application No. 16/747,315 is a continuation-in-part of application No. 15/424,732, filed on Feb. 3, 2017, now Pat. No. 10,543,338, said application No. 15/668,266 is a continuation-in-part of application No. 13/801,750, filed on Mar. 13, 2013, now Pat. No. 9,808,647.

(60) Provisional application No. 62/292,028, filed on Feb. 5, 2016, provisional application No. 61/686,432, filed on Apr. 5, 2012.

(51) Int. Cl.
*A61M 39/10* (2006.01)
*A61N 5/067* (2006.01)

(52) U.S. Cl.
CPC ............... *A61N 2005/063* (2013.01); *A61N 2005/0659* (2013.01); *A61N 2005/0663* (2013.01)

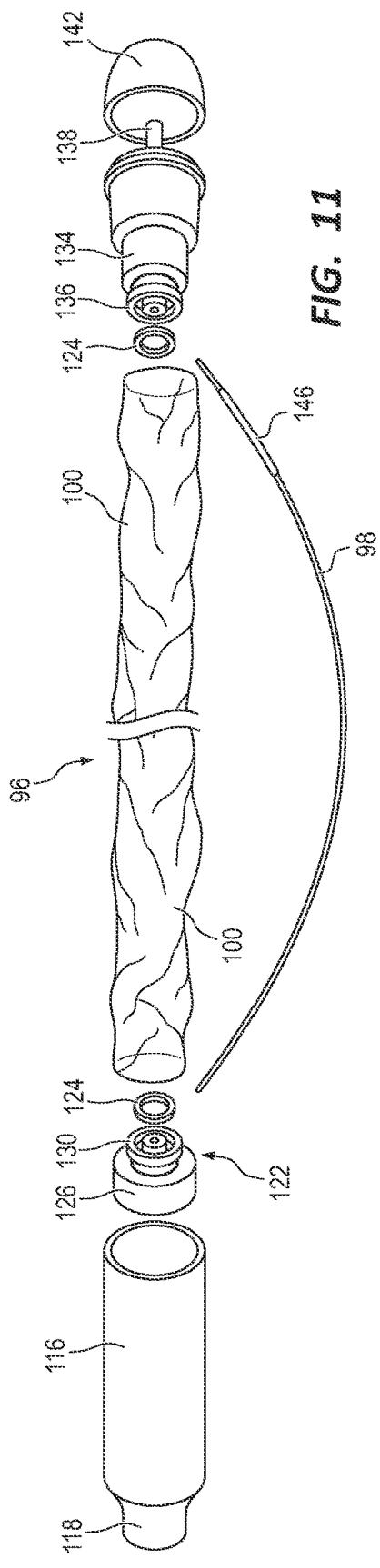
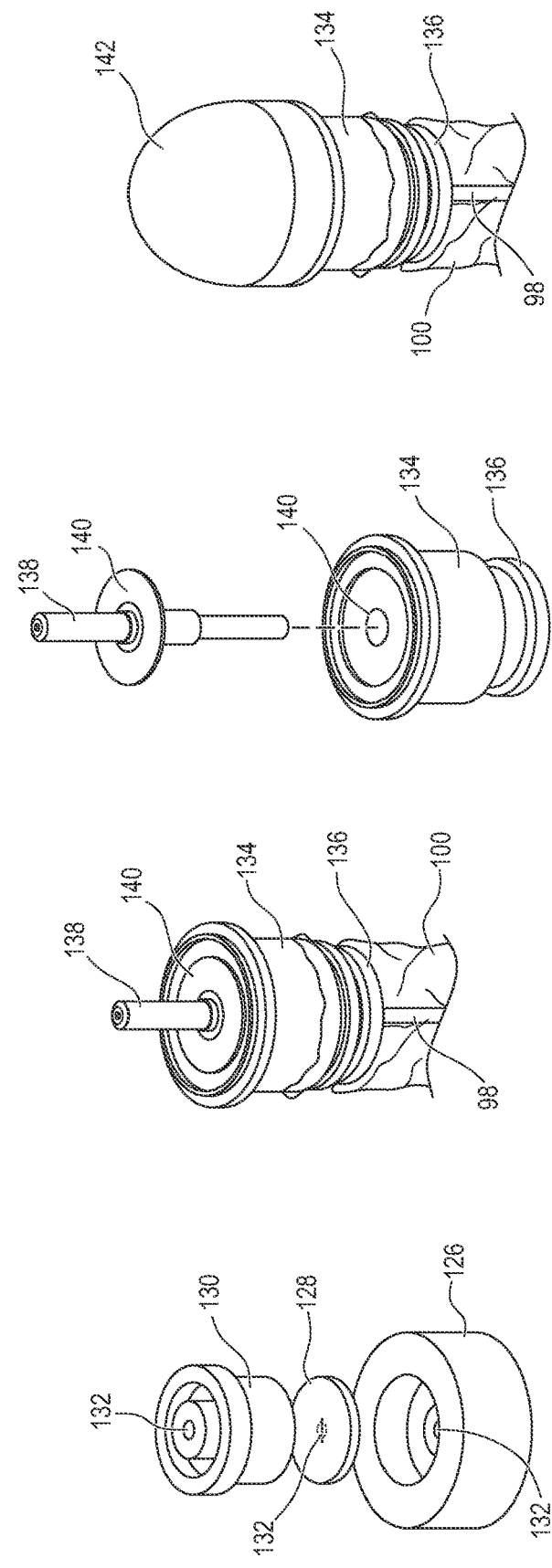

LIGHT DELIVERY SYSTEM WITH A FIBER OPTIC DISPOSABLE FOR PREVENTING, REDUCING AND/OR ELIMINATING INFECTIONS DURING INSTITUTIONAL OR IN-HOME USE

RELATED APPLICATIONS

This application is a continuation of U.S. patent application Ser. No. 17/579,657, filed Jan. 20, 2022 and titled ELECTROMAGNETIC RADIATION DELIVERY AND MONITORING SYSTEM AND METHODS FOR PREVENTING, REDUCING AND/OR ELIMINATING CATHETER-RELATED INFECTIONS DURING INSTITUTIONAL OR IN-HOME USE, which is a continuation-in-part of U.S. patent application Ser. No. 16/364,051, filed Mar. 25, 2019 and titled METHODS AND APPARATUS TO DELIVER THERAPEUTIC, NON-ULTRAVIOLET VERSATILELY VIA A CATHETER RESIDING IN A BODY CAVITY (hereinafter the "Parent Application"), which is a continuation-in-part of U.S. patent application Ser. No. 15/668,266, filed Aug. 3, 2017 and titled METHODS AND APPARATUS TO DELIVER THERAPEUTIC, NON-ULTRAVIOLET ELECTROMAGNETIC RADIATION TO INACTIVATE INFECTIOUS AGENTS AND/OR TO ENHANCE HEALTHY CELL GROWTH VIA A CATHETER RESIDING IN A BODY CAVITY (hereinafter the "Grandparent Application") now issued as U.S. Pat. No. 10,307,612, on Jun. 4, 2019, which is a continuation-in-part of U.S. patent application Ser. No. 13/801,750, filed Mar. 13, 2013 and titled METHODS AND APPARATUS TO INACTIVATE INFECTIOUS AGENTS ON A CATHETER RESIDING IN A BODY CAVITY (hereinafter the "Great-Grandparent Application"), now issued as U.S. Pat. No. 9,808,647 on Nov. 7, 2017, which claimed the benefit of U.S. Provisional Application No. 61/686,432 filed Apr. 5, 2012 and was entitled HINS LASER LIGHT CATHETER. This application also is a continuation-in-part of U.S. patent application Ser. No. 17/000,736, filed Aug. 24, 2020, and titled METHODS AND APPARATUS TO DELIVER THERAPEUTIC, NON-ULTRAVIOLET ELECTROMAGNETIC RADIATION IN A DIALYSIS SYSTEM (hereinafter the "Second Parent Application"), which is a continuation-in-part of the Parent Application, U.S. patent application Ser. No. 16/364,051, filed Mar. 25, 2019 and titled METHODS AND APPARATUS FOR REMOVABLE CATHETER VISUAL LIGHT THERAPEUTIC SYSTEM ELECTROMAGNETIC RADIATION VERSATILELY VIA A CATHETER RESIDING IN A BODY CAVITY. Additionally, this application also is a continuation-in-part of U.S. patent application Ser. No. 16/747,315, filed Jan. 20, 2020 and titled METHOD AND APPARATUS FOR REMOVABLE CATHETER VISUAL LIGHT THERAPEUTIC SYSTEM (hereinafter the "Third Parent Application"), which is continuation-in-part of U.S. patent application Ser. No. 15/424,732, filed Feb. 3, 2017 and titled METHOD AND APPARATUS FOR REMOVABLE CATHETER VISUAL LIGHT THERAPEUTIC SYSTEM, now issued as U.S. Pat. No. 10,543,338 on Jan. 28, 2020, which claimed the benefit of U.S. Provisional Application No. 62/292,028 filed Feb. 5, 2016, and entitled METHOD AND APPARATUS FOR REMOVABLE CATHETER VISUAL LIGHT STERILIZATION SYSTEM. Each of the related applications referred to in this paragraph is hereby incorporated by this reference as if fully set forth herein.

TECHNICAL FIELD

The present invention is a method and apparatus to provide versatile delivery and monitoring of therapeutic doses of non-ultraviolet light to inactivate infectious agents residing on, within, or generally around a catheter while the catheter is residing within a body cavity or residing on, within, or around extension catheters and connectors outside the body along the flow path of fluids such as dialysate and waste dialysate, blood, urine, medicating fluids, and the like, and to stimulate healthy cell growth within the body and at the entry/exit site causing a healing effect.

Such versatile delivery of therapeutic doses of non-ultraviolet light may employ controlled relative intensity and/or treatment region specific application of the therapeutic doses. This disclosure is of a medical device assembly, and particularly a light-energy source and delivery components (sometimes including a disposable fiber optic introducer), that utilizes non-ultraviolet visual therapeutic electromagnetic radiation (EMR) at a high enough intensity to stimulate healthy cell growth causing a healing effect and/or to reduce or eliminate infectious agents in, on, and around a catheter while the catheter resides inside a body cavity and/or in, on, and around the extension catheters and connectors outside the body along the flow path of fluids such as dialysate and waste dialysate.

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "some embodiments," "various embodiments," and the like, may indicate that the embodiment(s) of the invention so described may include a particular feature, structure, or characteristic, but not every embodiment necessarily includes a particular feature, structure, or characteristic. Further, repeated use of the phrase "in one embodiment," or "in an exemplary embodiment," do not necessarily refer to the same embodiment, although they may.

BACKGROUND

Catheters are tubular structures commonly used as channels to inject medications into or retrieve fluid samples from a patient. Each catheter comprises a tube, usually derived from plastic or other polymers, such as silicone, polyurethane, and the like, that at least a portion thereof may be inserted into an area of the body and may contain one or more separate lines in which these fluids may be delivered or retrieved. A "lumen" designates a pathway in the catheter that goes from outside the body to inside the body. Catheters and other tubular structures are used in various applications, including intravascularly, abdominally, urologically, gastrointestinally, ophthalmically, within the respiratory tract, within cranial space, within the spinal column, during dialysis and the like. In all cases, the catheter extends from outside the body to be placed inside of a space in the body where the catheter or a portion of a catheter assembly resides, herein referred to as a "body cavity". These devices frequently give rise to infections caused by growth of infectious agents in, on, and around the catheter and on tissue surrounding the catheter. Infectious agents can include bacteria, fungi, viruses, or the like that enter the body and lead to illness of a patient. Depending on the location of the catheter placement, these infections can arise in the form of urinary tract infections, blood stream infections, soft tissue infection, and the like.

Catheter related infections (CRIs) are a large problem in medicine, leading to high morbidity and mortality rates. Current methods of reducing or eliminating the number of infectious agents in, on, around a catheter are of low efficacy. Typically, catheters will be removed if they are suspected to be harboring infectious agents, increasing both the cost associated with treatment and patient discomfort. Various methods to deter or eliminate growth of infectious agents in, on, and around catheters have been attempted, such as using sterile handling techniques, antibiotics, and replacing the catheter when an infection is suspected. Despite these techniques, infections resulting from catheters remain a major problem. According to the Centers for Disease Control and Prevention, over 31,000 people died specifically from catheter-related bloodstream infections in 2010. These infections, along with urinary tract infections, gastrointestinal infections, dialysis-related infections and other infections from catheters, increase medical costs, insurance costs, and patient discomfort.

Catheters come in various sizes. Those that are smaller in diameter, such as many PICC lines (peripherally inserted central catheters), have small diameter lumens. Such smaller diameter catheters may be suitable for prolonged insertion. Consequently, with smaller diameter catheters, there may be inadequate thickness to the catheter wall to carry a sterilization and/or healthy growth enhancing delivery system.

The use of ultraviolet (UV) light, disinfecting chemicals, catheters impregnated with drugs, to name a few, have been attempted to reduce the prevalence of infection. Many patents have attempted to utilize UV light to disinfect catheters. Unfortunately, UV light is well known to cause damage to living cells. Methods to disinfect connectors, stopcocks, and valves using the projection of sterilizing electromagnetic radiation (EMR) have also been attempted using 405 nm light to sterilize these points, but these methods neglect disinfection of the catheter body as well as the tip of the catheter.

The emergence of infectious agents that are resistant to current treatments, such as methicillin-resistance *Staphylococcus aureus* (MRSA), further substantiate the need for another treatment of CRIs. To reduce the costs associated with removing and replacing the catheters from and into the patient, there is a need for sterilization of the entire catheter or catheter assembly while at least a portion of the catheter resides in the patient. Additionally, it would be advantageous to be able to stimulate healthy cell growth by providing therapeutic EMR via such indwelling catheters.

Immediate disinfection after placement could help prevent growth of undesirable biofilm on the catheter. Biofilm comprises extracellular polymeric material created by microorganisms after they adhere to a surface. This biofilm facilitates the growth of infectious agents and is very difficult to break down once it has begun to grow.

The growth of infectious agents can result from agents outside the patient (contamination during handling, at the point of access as the catheter penetrates or crosses the skin, from the catheter hub, or from any other exterior contamination) or from inside the patient, wherein infectious agents already in the body attach to the surface of the catheter and proliferate. Scientific literature suggests that approximately 65% of CRI's come from infectious agents residing on the skin of the patient (S. Öncü, Central Venous Catheter—Related Infections: An Overview with Special Emphasis on Diagnosis, Prevention and Management. The Internet Journal of Anesthesiology. 2003 Volume 7 Number 1). These agents travel down the outside of the catheter and colonize the catheter tip. For short term catheterization, this is believed to be the most likely mechanism of infection (Crump. Intravascular Catheter-Associated Infections. Eur J Clin Microbiol Dis (2000) 19:1-8). Thirty percent (30%) of CRIs are believed to come from a contaminated hub, in which infectious agents travel down the interior of the catheter (Öncü). This is believed to be the most likely mechanism of infection for long-term catheterization (Crump).

EMR in the range of 380-900 nm has been shown to be effective in killing infectious agents. Research done by a group at the University of Strathclyde shows that light in this range is effective in killing surface bacteria in burn wards without harming the patients (Environmental decontamination of a hospital isolation room using projected high-intensity light. J Hosp Infect. 2010 November; 76(3):247-51). Published patent application 2010/0246169, written by the members who conducted the study, utilizes ambient lighting to disinfect a large surrounding area. The mechanism proposed by the team suggests that light in this range leads to photosensitization of endogenous porphyrins within the bacteria, which causes the creation of singlet oxygen, leading to the death of the bacteria. (Inactivation of Bacterial Pathogens following Exposure to Light from a 405-Nanometer Light-Emitting Diode Array. Appl Environ Microbiol. 2009 April; 75(7):1932-7).

Heretofore, however, there has never been apparatus or methods for making or using such apparatus to disinfect a catheter safely and effectively while it is still implanted in a patient. Accordingly, there exists a need for methods and apparatus designed to deliver non-antibiotic, bactericidal therapeutics in-vivo. Such methods and apparatus, using novel technology, may provide removable delivery of safe, effective, and reproducible disinfection and/or enhance healthy cell growth.

SUMMARY OF THE INVENTION

The exemplary embodiments of this disclosure relate to medical device assemblies for insertion into a cavity of a patient's body and for delivery from outside the body to inside the body and retrieval of fluids from inside the body to outside the body. Each assembly comprises an electromagnetic radiation (EMR) source for providing non-ultraviolet, therapeutic EMR having intensity sufficient to inactivate one or more infectious agents and/or to enhance healthy cell growth. Each assembly either comprises a catheter, a catheter extension, or may be used with a catheter having an elongate catheter body with at least one internal lumen, a coupling end, and a distal end. This distal end is insertable into the cavity of the patient's body whether the cavity is venous, arterial, gastrointestinal, abdominal, urological, respiratory, cranial, spinal, or the like, wherein the indwelling catheter body may direct the fluid and/or the propagation of the therapeutic EMR axially relative to the catheter body for radial delivery into a catheter extension or the catheter, into the patient's body and/or at the distal end. Also, when appropriate, the therapeutic EMR may be directed at or into catheter extensions and connectors outside the body at or into the insertion area. An optical element disposed within a lumen of the catheter body and/or within the catheter body acts conducive to the axial propagation of the therapeutic EMR relative to the catheter body. The optical element or another optical element also may be disposed to act conducive to propagation of therapeutic EMR through at least one coupling element to connect the EMR component to the insertable catheter component.

For the purposes of this disclosure the use of the term "therapeutic" should be understood to mean; of or relating to the treatment of disease, including reducing or eliminating infectious agents, as well as serving or performed to maintain health, including enhancing healthy cell growth.

For the purpose of this disclosure the use of the phrase "controlled relative intensity" should be understood to be a term of versatility meaning that the delivery of EMR at various desired intensities may be controlled in any of a number of ways such as 1) by using different single fibers; 2) by using different radial-emission locations and/or gradients; 3) by using multiple differing fibers; and 4) by retro-fitting the fiber type and/or design for tailored use with an existing catheter or catheter extensions. The versatility contemplated by the phrase "controlled relative intensity" is the ability to deliver EMR of the desired/appropriate intensities to desired location(s) at time(s) most effective within the broad range of types and sizes of catheters.

For the purpose of this disclosure the use of the phrase "treatment region specific" should be understood likewise to be a term of versatility meaning that the delivery of EMR at various desired intensities for desired dosing may be delivered to specific treatment regions by utilizing fiber(s) with radial-emission capability compatible with the specific region or regions within the patient's body and/or in, on, or around the catheter or catheter extensions and connectors to be treated by the application of EMR.

The exemplary medical device assembly comprises an EMR source, an EMR conduction system, and at least one coupling to connect the EMR source to the EMR conduction system. The EMR source provides non-ultraviolet, therapeutic EMR having intensity sufficient to inactivate one or more infectious agents and/or to stimulate healthy cell growth causing a healing effect. In at least one exemplary embodiment, the EMR conduction system may be at least partially insertable into and removable from the lumen of an indwelling catheter or a catheter extension. Because the EMR conduction system is removably insertable, in yet another exemplary embodiment, a differing, second EMR conduction system (or at least the optical element of a second EMR conduction system) may also be removably insertable such that the two differing EMR conduction systems may be interchangeably insertable into the same lumen of the catheter or into the extended lumen of the catheter and into catheter extension(s).

In some exemplary embodiments, methods and apparatuses are provided for effectively sterilizing a catheter and the area surrounding the catheter while the catheter is disposed in a body cavity. Such medical device assemblies use sterilizing EMR to reduce or eliminate the count of infectious agents in, on, or around the catheter and/or on or in tissue surrounding the catheter while in a body cavity. In other exemplary embodiments, systems (such as dialysis systems) may have catheter extensions (e.g., fluid extension lines) and connectors disposed outside the body for which effective sterilizing thereof enhances the prevention, reduction, and elimination of infectious agents throughout the system, including in, on, or around the catheter, in, on, or around catheter extensions or connectors, and/or on or in tissue surrounding the catheter while in a body cavity.

The EMR source can be from a single, multiple, or group of EMR sources including, but not limited to, a light emitting diode, a semiconductor laser, a diode laser, an incandescent (filtered or unfiltered) and a fluorescent (filtered or unfiltered) light source. This EMR source (or multiple sources) provides non-ultraviolet, therapeutic EMR providing one or more wavelengths in the range of above 380 nm to about 904 nm. To provide sufficient inactivation of infectious species and/or stimulation of healthy cell growth, each EMIR wavelength should be of a narrow spectrum and centered around one wavelength from the group. The intensity should be sufficient to inactivate one or more infectious agents and/or to stimulate healthy cell growth causing a healing effect. This group includes several wavelengths centered about: 400 nm, 405 nm, 415 nm, 430 nm, 440 nm, 445 nm, 455 nm, 470 nm, 475 nm, 632 nm, 632.8 nm, 640 nm, 650 nm, 660 nm, 670 nm, 680 nm, 780 nm, 808 nm, 830 nm, and 904 nm.

The EMR source may require drivers and electronic support for full functionality. Consideration should be given to accommodating the support hardware and/or software, which may encompass a significant portion of the EMR source's functionality and efficacy. It is possible that the EMR source may generate heat, which could be detrimental to the EMR source and may need to be limited or dampened.

This disclosure describes a catheter (or a catheter assembly) having an elongate catheter body with at least one internal lumen, a coupling end and a distal end, the distal end being insertable into the cavity of the patient's body. The catheter body is meant to direct both the fluid and the therapeutic EMIR axially relative to the catheter body for delivery into the patient's body at the insertion site, along the elongate catheter body, and/or at the distal end. This disclosure includes an optical element disposed within the catheter body and conducive to the axial propagation of the therapeutic EMR through the catheter body. Finally, this disclosure describes at least one coupling element to connect the radiation source to the catheter body. Further, the catheter may be connected to one or more extension catheters (e.g., fluid extension lines) and connectors through which fluid is supplied or retrieved. It may be advantageous to have such extension catheters and connectors also be conducive to the axial propagation of the therapeutic EMR therethrough so that the delivery of therapeutic EMIR may enhance the prevention, reduction, and elimination of infectious agents within the overall system.

The sterilizing EMIR is transmitted down a specialized path within the catheter via an optical element conducive to the axial propagation of the light. Various methods could be used to facilitate axial propagation of the light relative to the catheter, including a reflective coating within a line of the catheter, a fiber optic cable, a lens, a waveguide, or the like. The light source can be a light-emitting diode (LED), laser, fiber optic filament, or the like.

One exemplary embodiment of the EMR source and support components is simplified to contain only the EMR source and necessary components. In another exemplary embodiment of the EMIR conduction system, a passive heat sink is required to diffuse the heat generated into the surrounding environment. In yet another exemplary embodiment of the EMR source, a heat sink may be coupled to at least one fan to actively dissipate heat generated by the EMR source. In other embodiments, multiple EMR sources connected to separate individual optical elements or a single EMR source capable of connecting to separate individual optical elements and providing EMIR of distinctly different intensities and/or wavelengths to separate optical elements may be employed.

Of particular interest to this disclosure is the use of light between 380 nm and about 900 nm wavelengths. Additionally, the intensity and power of the light emitted bear significantly on the inactivation of infectious agents, thus a range of radiant exposures covering 0.1 $J/cm^2$ to 5 $kJ/cm^2$ (or in some instances up to 10 $kJ/cm^2$), and a range of powers from 0.005 mW to 5 W (or in some instances up to 10 W), and power density range covering 1 mW/cm$^2$ and 2 W/cm$^2$ (or in some instances up to 5 W/cm$^2$), are of interest for these exemplary device assemblies and methods. These ranges of wavelengths, power densities, and radiant exposures have been shown to have either antimicrobial effects or positive biological effects on healing tissue. These positive biological effects include reduction of inflammatory cells, increased proliferation of fibroblasts, stimulation of collagen synthesis, angiogenesis inducement and granulation tissue formation.

For each exemplary embodiment described herein, the EMR conduction system and method for disinfection/healing could be utilized in manually or CPU controlled adjustable or predetermined duty cycle. If treatments begin immediately after sterile procedure was initiated, device related infections may be inhibited or prevented. This includes device-related biofilm growth.

A treatment may include at least one wavelength of therapeutic EMR that acts as a predominant wavelength selected to sterilize one or more target organisms and selected from the group of wavelengths centered about 400 nm, 405 nm, 415 nm, 430 nm, 440 nm, 445 nm, 455 nm, 470 nm, 475 nm, 660 nm, and 808 nm, or a predominant wavelength selected to promote healing and healthy cell growth may be selected from the group of wavelengths centered about 632 nm, 632.8 nm, 640 nm, 650 nm, 660 nm, 670 nm, 680 nm, 780 nm, 808 nm, 830 nm, and 904 nm. Another treatment may include alternating the predominant wavelength between a first predominant wavelength and a second predominant wavelength (differing from the first predominant wavelength) in a selected treatment pattern. Further, sterilizing EMR and EMR that stimulates healthy cell growth may be transmitted alternatingly, simultaneously, in tandem. or alternatively.

A method for constructing an exemplary medical device assembly for insertion into a cavity of a patient's body and for delivery of a fluid (such as a dialysate, a saline solution, or hemodialysis freshened blood) to or retrieval of a fluid (such as waste dialysate or unfreshened blood) from the patient's body may comprise the steps of: locating an indwelling catheter or providing a catheter having an elongate catheter body with one or more internal lumens, a coupling end and an distal end, the distal end being previously inserted/insertable into the cavity of the patient's body; applying one or more optical elements within one or more lumens of the catheter body (or an extension catheter) and/or within a wall of the catheter body, the optical element being conducive to the axial propagation of therapeutic EMR relative to the catheter body; and coupling at least one EMR source to the EMR conduction system and/or the catheter body (or an extension catheter), the EMR source for providing non-ultraviolet, therapeutic EMR having an intensity sufficient to inactivate one or more infectious agent and/or to enhance healthy cell growth.

In one exemplary embodiment, the device uses a catheter that is inserted into a cavity of a patient's body, wherein said catheter allows both fluid and therapeutic EMR to travel axially relative to the catheter body. The catheter also contains at least one coupling lumen to connect an EMR source that will transmit the therapeutic EMR through the coupling lumen and axially relative to the catheter line. A coupling element in this context will usually refer to a typical hub on the therapeutic EMR source.

In at least one exemplary embodiment, a removably insertable EMR conduction system (i.e., an EMR conduction system that may be partially or fully inserted into a lumen of a catheter and may also be partially or fully extracted from disposition within a lumen of a catheter) may comprise at least one optical element having an elongate body conducive to the axial propagation of the therapeutic EMR through the elongate body. This elongate body may have an exterior surface between a coupling end and a distal end. The exterior surface may have at least one radial emission portion wherein the radial emission facilitates the radial emission of therapeutic EMR from the elongate body proximate each radial emission portion. Again, because the removably insertable EMIR conduction system may be fully extracted from within a lumen of the catheter, in another exemplary embodiment, a differing, second removably insertable EMIR conduction system (or at least the optical element of a second EMR conduction system) may be interchangeably insertable into the same lumen of the catheter. The second removably insertable EMR conduction system may differ in that it may have at least one radial emission portion that differs from at least one radial emission portion of the interchangeable EMR conduction system.

At least one coupling connects the radiation source to the EMR conduction system and, in some exemplary embodiments, may comprise at least one feature that allows for the coupling to be readily removable from the EMR conduction system. The exemplary coupling may be achieved by utilizing a uniquely designed connection, a pre-manufactured coupling system, or any combination thereof that optimizes the coupling efficiency and utility. Further, such couplings couple the removably insertable EMR conduction system to the EMR source and may comprise more than one coupling with an intermediate section optimized to further the propagation of the EMR. In one exemplary embodiment, the EMR source may be coupled to a patch cable or EMR conduction extending segment, which is then coupled to the formal removably insertable EMR conduction system.

The optical element further may comprise at least one optical feature selected from a group of optical features such as a reflective surface, an optically transmissible material, a lens, a fiber optic filament, and any combination thereof. The optical element also may be capable of transmitting more than one wavelength or intensity EMR, for example, the optical element may comprise one or more elongate bodies, with each elongate body transmitting a different wavelength and/or intensity of EMR. Multiple wavelengths may be transmitted alternatively, simultaneously, alternatively, or in tandem, or a combination thereof (for example, one constantly on and the other wavelength pulsed). Multiple intensities may be transmitted through the same element simultaneously. Alternating patterns of light treatments may also be transmitted.

The EMR conduction system may be configured to insert, at least partially, into one of any number of tubular structures such as catheters, that as by way of example only and not to be limiting, includes a central venous catheter, a peripheral insertion catheter, a peripheral insertion central catheter, a midline catheter, a jugular catheter, a subclavian catheter, a femoral catheter, a cardiac catheter, a cardiovascular catheter, a urinary Foley catheter, an intermittent urinary catheter, an endotracheal tube, a dialysis catheter with or without extension tubing connected thereto (whether hemodialysis or peritoneal dialysis (see FIGS. 14A to 22A)), a gastrointestinal catheter, a nasogastric tube, a wound drainage catheter, or any similar accessing medical catheter or tube that has been inserted into a patient or is connected to a catheter or tube for the purpose of delivering or retrieving fluids or samples via an inserted catheter or tube.

One exemplary embodiment of the EMR conduction system has an optical element comprising a single, insertable optical fiber. With a single optical fiber, the single fiber may allow light to transmit radially or axially at various sections along its length. For sections where light will transmit radially, the exterior surface of the optical element may be altered to facilitate the radial emission of the EMR. The alteration of the exterior surface may be achieved by chemical etching, physical etching, or electromagnetic ablation through plasma or lasers to create various radial emission portions along the length of the optical fiber. The radial emission portions permit light to emit radially from the optical fiber. Of course, another exemplary embodiment of the EMR conduction system may comprise multiple single, insertable optical fibers, each being of the same length or differing lengths, or inserted partially or fully into a catheter or a catheter extension.

For purposes of this disclosure, light emitted radially means that the light has a radial component. Hence, the light emitted radially may emit perpendicularly and/or obliquely to the central axis of the optical fiber at the axial point of emission.

For embodiments having radial emission sections, the material comprising the optical fiber may be selected from a group of materials comprising optical fibers including plastic, silica, fluoride glass, phosphate glass, chalcogenide glass, and any other suitable material that is capable of axial light propagation and surface alteration to achieve radial emission. In addition, the optical fibers may be single mode, multi-mode, or plastic optical fibers that may have been optimized for alteration using a chemical, physical, or electromagnetic manufacturing alteration process. The optical fibers may also be optimized for alteration post-production.

Yet another exemplary embodiment employs a physical abrasion method of alteration to modify the EMIR conduction system comprised of at least one optical fiber. This fiber would be utilized based on its optimal optical response to the physical abrasion process. This process may include, but is not limited to, sanding, media blasting, grinding, or buffing at least one section of the optical fiber. The physical abrasion process would also necessarily be optimized in terms of the extent of physical abrasion to optimize the appropriate radial EMR emission or lack thereof. This may be accomplished by adjusting at least one of velocity, acceleration, pressure, modification time, or abrasion material utilized in modifying the optical fiber.

Yet another exemplary embodiment employs microscopic porous structures suspended within the optical fiber to achieve radial transmission of light. These microscopic structures may be positioned within the core and/or core-cladding boundary of the optical fiber. The microscopic structures having a refractive index lower than the region free of microscopic structures. The microscopic structures may be a material added to the optical fiber core or the core-cladding boundary, such as a metal, rubber, glass, or plastic. The microscopic structures may also be the lack of material creating an aberration within the optical fiber core or the core-cladding boundary. For example, the presence of microscopic bubbles in the optical fiber core would create an aberration or imperfection that would alter the materials refractive index, resulting in EMR being emitted radially from the optical fiber.

Another exemplary embodiment may comprise at least one optical fiber with cladding altered to optimize the radial or axial propagation of EMR. For example, the cladding may be altered to at least partially remove or thin the cladding to achieve partial radial transmission of EMR. Another example could include an optical fiber with only certain portions containing cladding, the EMIR transmitting axially in the clad portions and at least partially axially and radially in the non-clad portions.

Yet another exemplary embodiment achieves uniform radial transmission wherein the radial emission portion of the optical fiber has substantially equivalent intensity over the length of the radial emission portion along the optical fiber. This may be done through chemical etching, physical etching, plasma ablation, or laser ablation in a gradient pattern. By altering at least one of velocity, acceleration, pressure gradients, flow, modification time, or modification material or process, it is possible to achieve radial transmission equivalency throughout each portion or the entire length of the modified optical fiber. During manufacturing, a gradient-provided uniformity also may be achieved through addition of microscopic structures positioned within the core and/or core-cladding boundary in a gradient pattern. Also, radial transmission uniformity achieved through gradient cladding or core features are contemplated for achieving desired radial emission, whether substantially uniform over a portion length or varying as desired.

Still another exemplary embodiment achieves a gradient radial transmission wherein at least one portion of the optical fiber emits EMIR radially in a gradient distribution. The gradient distribution may also be accomplished through chemical etching, physical etching, plasma or laser ablation in a uniform or gradient pattern. By altering at least one of velocity, acceleration, pressure gradients, flow, modification time, or modification material or process, it is possible to achieve a gradient radial transmission throughout a portion of the optical fiber. This may also be achieved through addition of microscopic structures positioned within the core and/or core-cladding boundary. Gradient radial transmission enables another exemplary embodiment to exhibit controlled relative intensity that may be uniform over a portion of the length and/or non-uniform and varying as desired.

A further exemplary embodiment of a removably insertable EMR conduction system comprises an optical element such as at least one LED, its associated wiring components, and a scaffold. The LED(s) may emit EMR based on the LED's inherent distribution, or may utilize another optical element, such as a lens or mirror, to focus or diffuse the EMR in the direction of interest. In addition, more than one LED could be arranged in an array to appropriately emit EMR for maximal therapeutic benefit. The LED(s), together with associated wiring components may be permanently or removably attached to the scaffold, which allows for removable insertion of the EMR conduction system into a catheter. The scaffold may be rigid, semi-rigid, malleable, elastic, or flexible, or any combination thereof.

In another exemplary embodiment, a catheter with multiple lumens for fluid injection or retrieval contains one or more separate lumens for transmission of the therapeutic EMR. Each lumen may have a separate proximal catheter hub assembly. These internal lumens converge at a convergence chamber, where individual internal lumens consolidate into a single elongated catheter body while retaining their individual internal paths. Such exemplary device may include use of an optical method for diverting the radiation between the convergence chamber and axially through the designated catheter internal lumen.

Samples retrieved through the distal end are often used to characterize the type of infection. One exemplary embodiment of the disclosure focuses on maintaining axial propagation of the light relative to the catheter and delivering therapeutic light of sufficient intensity to the distal end of the catheter to prevent, reduce or eliminate the count of infectious agents residing thereon.

In yet another exemplary embodiment, the medical device assembly would be used in a urological setting. The catheter (such as a Foley catheter) would be placed into the urethra and bladder of the urinary tract.

In yet another exemplary embodiment, the medical device assembly would be used in a gastrointestinal setting.

In yet another exemplary embodiment, the medical device assembly would be used in an intravascular setting.

In yet another exemplary embodiment, the medical device assembly would be used within the cranial cavity of a patient.

In yet another exemplary embodiment, the medical device assembly would be used within the spinal cavity of a patient.

In still another exemplary embodiment, the medical device assembly would be used within an ophthalmic cavity of a patient.

In still another exemplary embodiment, the medical device assembly would be used within a dialysis catheter with or without extension catheter(s) and/or connector(s) (whether hemodialysis or peritoneal dialysis).

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the present disclosure will be described with additional specificity and detail through use of the accompanying drawings in which:

FIG. 11 is an exploded view of the fiber optic disposable of FIG. 9, showing various component parts thereof.

FIG. 11A is an exploded view of an exemplary check valve shown as one of the components of the fiber optic disposable of FIG. 9.

FIG. 11B is a reversed perspective view of an exemplary ferrule assembly shown as one of the components of the fiber optic disposable of FIG. 9.

FIG. 11C is an exploded perspective view of the exemplary ferrule assembly shown as one of the components of the fiber optic disposable of FIG. 9, showing various components of the ferrule assembly.

FIG. 11D is a reversed perspective view of an exemplary ferrule cover shown as one of the components of the fiber optic disposable of FIG. 9.

FIG. 14A is a perspective view of an exemplary two-cuff peritoneal dialysis catheter showing the radial emission extending from a connector hub and a point proximate to and downstream from the peritoneal cuff, FIG. 14B is a perspective view of another exemplary two-cuff peritoneal dialysis catheter showing the radial emission of EMR between a point upstream of the subcutaneous cuff and a point downstream of the peritoneal cuff, and FIG. 14C is a perspective view of yet another exemplary two-cuff peritoneal dialysis catheter showing the radial emission of EMR between the connector hub and a point within a peritoneal dialysis solution region.

Figure 1:
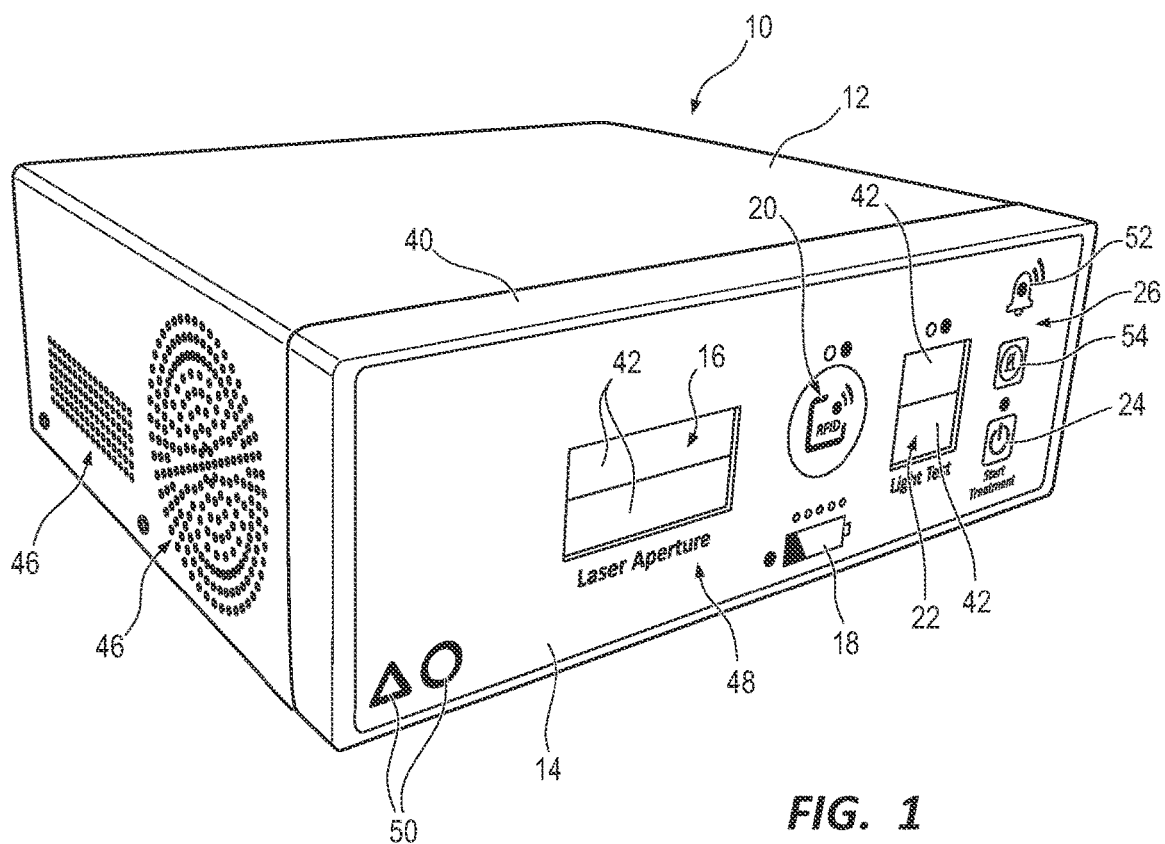
FIG. 1 is a perspective frontal view of an exemplary embodiment of a light engine box showing various features accessible from the front panel overlay of the light engine box, including a laser aperture, a battery power indicator, RFID feature, a light test aperture, treatment on/off actuator, and alarm features.

| REFERENCE NUMERALS | |
|---|---|
| (smart) light engine system 10 | light engine box 12 |
| front panel overlay 14 | laser aperture 16 |
| battery power indicator 18 | RFID feature 20 |
| light test aperture 22 | treatment on/off actuator 24 |
| alarm features 26 | back panel 28 |
| on/off switch 30 | power ports 32 |
| laser assembly 34 | central processing unit 35 |
| battery assembly 36 | side port test module 38 |
| front panel 40 | dust covers 42 |
| umbilical light transmission cable 44 | |
| venting features 46 | user interface 48 |
| warning icons 50 | alarm alert 52 |
| alarm on/off actuator 54 | side port test adapter 56 |
| cable adapter or SMA adapter 58 | distal connector 60 |
| proximal connector 62 | cable 64 |
| fiber optics 66 | wire(s) 68 |
| cable sleeve 70 | first optical interlock 72 |
| optical interlock connector 74 | proximal SMA 76 |
| securement magnet(s) 78 | proximal connector shell 80 |
| extended forward edge 81 | SMA adapter 82 |
| second optical interlock 84 | press-in ball joint(s) 86 |
| distal SMA 88 | distal connector shell 90 |
| front cover 92 | pins 94 |
| fiber optic disposable 96 | optical fiber 98 |
| collapsible/retractable sleeve 100 | proximal end 102 |
| distal end 104 | packaging 106 |
| RFID adhesive tag 108 | face seal blister packaging 110 |
| see-through blister face 112 | opaque backing 114 |
| barrel 116 | female luer adapter 118 |

| REFERENCE NUMERALS -continued | |
|---|---|
| male luer plug 120 | check valve 122 |
| capture ring 124 | check valve body 126 |
| check valve disk 128 | a check valve cap 130 |
| central bore 132 | barrel plug 134 |
| barrel plug cap 136 | ferrule 138 |
| magnetic washer 140 | ferrule cap 142 |
| optical fiber receiving bore 144 | reinforced end 146 |
| fiber optic introducer 148 | main line 150 |
| entry port 152 | exit port 154 |
| branching line 156 | side port 158 |
| clamp 160 | sealing cap(s) 162 |
| extension set 164 | PD catheter 166 |
| connector hub 168 | peritoneal cuff 170 |
| subcutaneous cuff 172 | coiled Tenckhoff 174 |
| external region 176 | tunneled region 178 |
| exit site location 180 | intra-peritoneal region 182 |
| peritoneal dialysis solution region 184 | extended PD catheter assembly 186 |
| Y-port adapter 188 | extension line tubing 190 |
| connecting luer 192 | Y-site/transfer region 194 |
| extension set region 196 | connection hub region 198 |
| holes 200 | peritoneal dialysis solution 202 |
| patient's body 204 | peritoneal dialysis system 206 |
| fluid extension line 208 | dialysate exchange switch 210 |
| dialysate supply bag 212 | waste dialysate retrieval bag 214 |
| extension connector 216 | extension line portal 218 |
| dialysate inlet 220 | waste dialysate outlet 222 |
| exchange selector 224 | feed line 226 |
| waste dialysate 228 | introducing adapter 230 |
| drainage line 232 | receiver adapter 234 |
| line clamp 236 | dual introducing multi-direction adapter 238 |
| dialysis access 240 | hemodialysis system 300 |
| hemodialysis unit 302 | dialyzer 304 |
| blood pump 306 | dialysate reservoir 308 |
| waste dialysate reservoir 310 | saline bag 312 |
| heparin pump 314 | air trap/air detector 316 |
| arterial-pressure monitor 318 | venous-pressure monitor 320 |
| inflow-pressure monitor 321 | inbound blood flow tubing 322 |
| outbound blood flow tubing 324 | outbound venous line (venous access) 326 |
| inbound arterial line (arterial access) 328 | saline line 330 |
| feed line 332 | drainage line 334 |
| Arrow A | Arrows B |
| Flow Arrows C | Inflow Arrow D |
| Drainage Arrow E | |

Exemplary embodiments of the present disclosure will be best understood by reference to the drawings, wherein like parts are designated by like numerals throughout. It will be readily understood that the components of the exemplary embodiments, as generally described and illustrated in the Figures herein, could be arranged and designed in a wide variety of different configurations. Thus, the following more detailed description of the exemplary embodiments of the apparatus, system, and method of the present disclosure, as represented in FIGS. 1 through 22A, is not intended to limit the scope of the invention, as claimed, but is merely representative of exemplary embodiments.

The phrases "attached to", "secured to", and "mounted to" refer to a form of mechanical coupling that restricts relative translation or rotation between the attached, secured, or mounted objects, respectively. The phrase "slidably attached to" refers to a form of mechanical coupling that permits relative translation, respectively, while restricting other relative motions. The phrase "attached directly to" refers to a form of securement in which the secured items are in direct contact and retained in that state of securement.

The term "abutting" refers to items that are in direct physical contact with each other, although the items may not be attached together. The term "grip" refers to items that are in direct physical contact with one of the items firmly holding the other. The term "integrally formed" refers to a body that is manufactured as a single piece, without requiring the assembly of constituent elements. Multiple elements may be formed integral with each other, when attached directly to each other to form a single work piece.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 2:
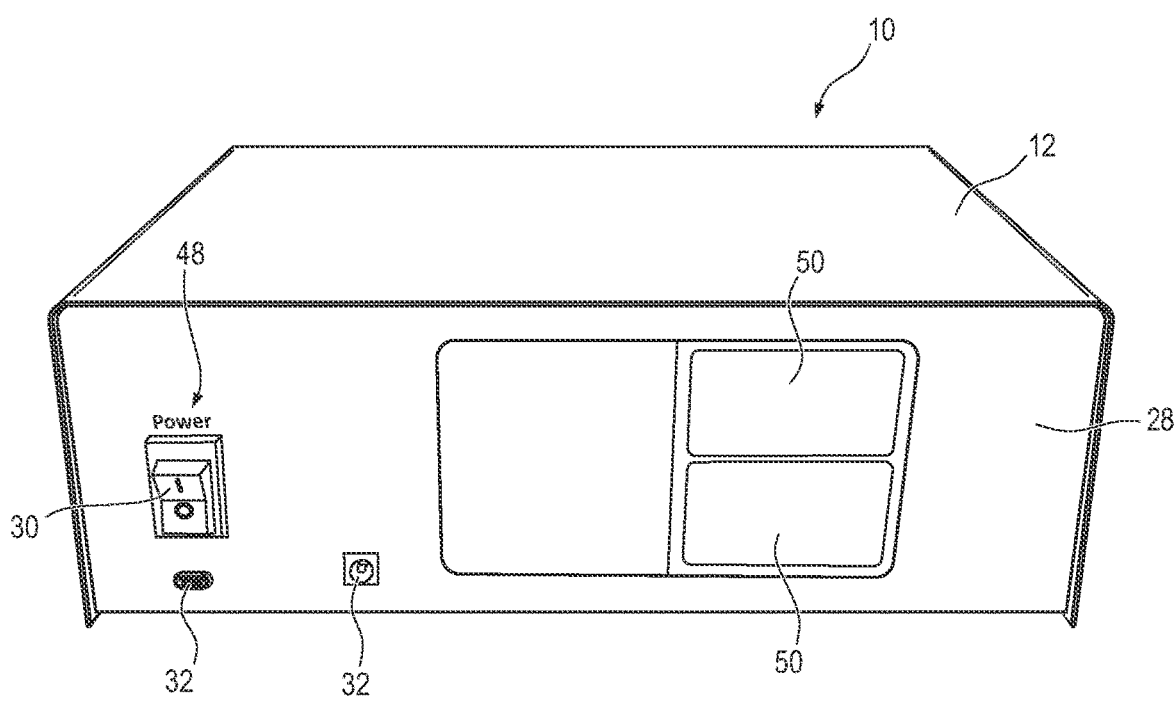
FIG. 2 is a perspective rear view of the exemplary embodiment of a light engine box showing various features accessible from the back panel of the light engine box, including an on/off switch and power ports.
Figure 3:
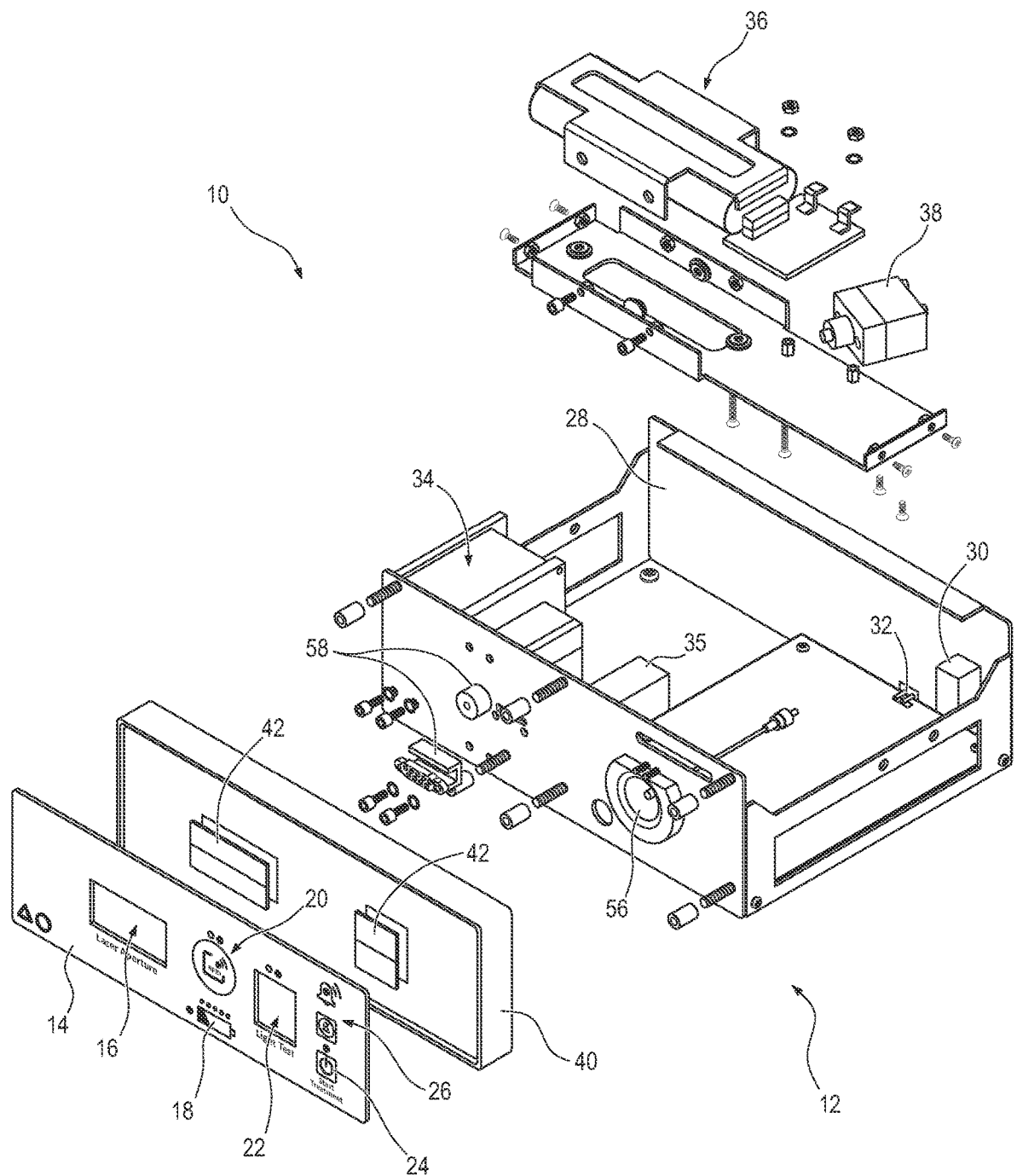
FIG. 3 is an exploded perspective view of an exemplary embodiment of a light engine box showing various component parts, including a laser assembly, a central processing unit (CPU), a battery assembly, a side port test module, a front overlay, and a front panel with dust covers.

FIGS. 1-5 are directed to a light engine system 10 (in this case a smart light engine system 10). FIG. 1 is a perspective frontal view of an exemplary embodiment of the smart light engine system 10 comprising a light engine box 12 showing various features accessible from a front panel overlay 14 of the light engine box 12, including a laser aperture 16, a battery power indicator 18, RFID feature 20, a light test aperture 22, treatment on/off actuator 24, and alarm features 26. FIG. 2 is a perspective rear view of the light engine box 12 of FIG. 1 showing various features accessible from a back panel 28 of the light engine box 12, including an on/off switch 30 and power ports 32. FIG. 3 is an exploded perspective view of the smart light engine system 10 of FIG. 1 showing various component parts, including a laser assembly 34, a central processing unit (CPU) 35, a battery assembly 36, a side port test module 38 having a photo diode (not shown), the front panel overlay 14 and a front panel 40 with dust covers 42. Other component parts will be referenced and described below.

Figure 4:
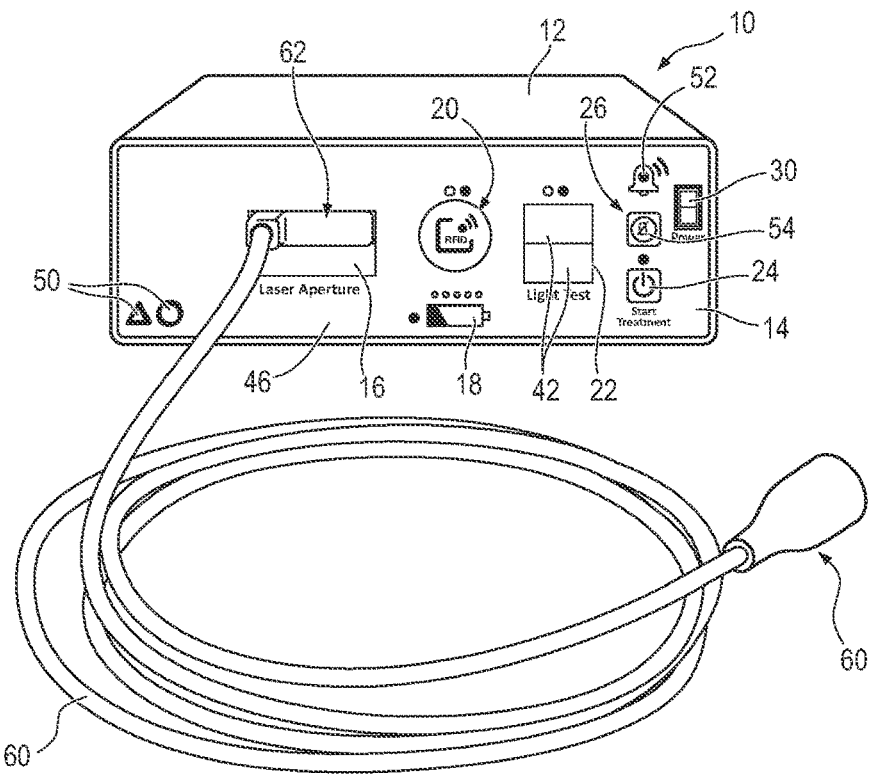
FIG. 4 is a perspective frontal view of another exemplary embodiment of a light engine box having an on/off switch on the front panel overlay and with an umbilical light transmission cable connected to the light engine box through the laser aperture and ready for use.

FIG. 4 is a perspective frontal view of an alternative exemplary embodiment of a light engine box 12 having the on/off switch 30 on the front panel overlay 14 and showing an exemplary umbilical light transmission cable 44 connected to the light engine box 12 through the laser aperture 16 and ready for use. The umbilical light transmission cable 44 will be referenced and described below.

Figure 5:
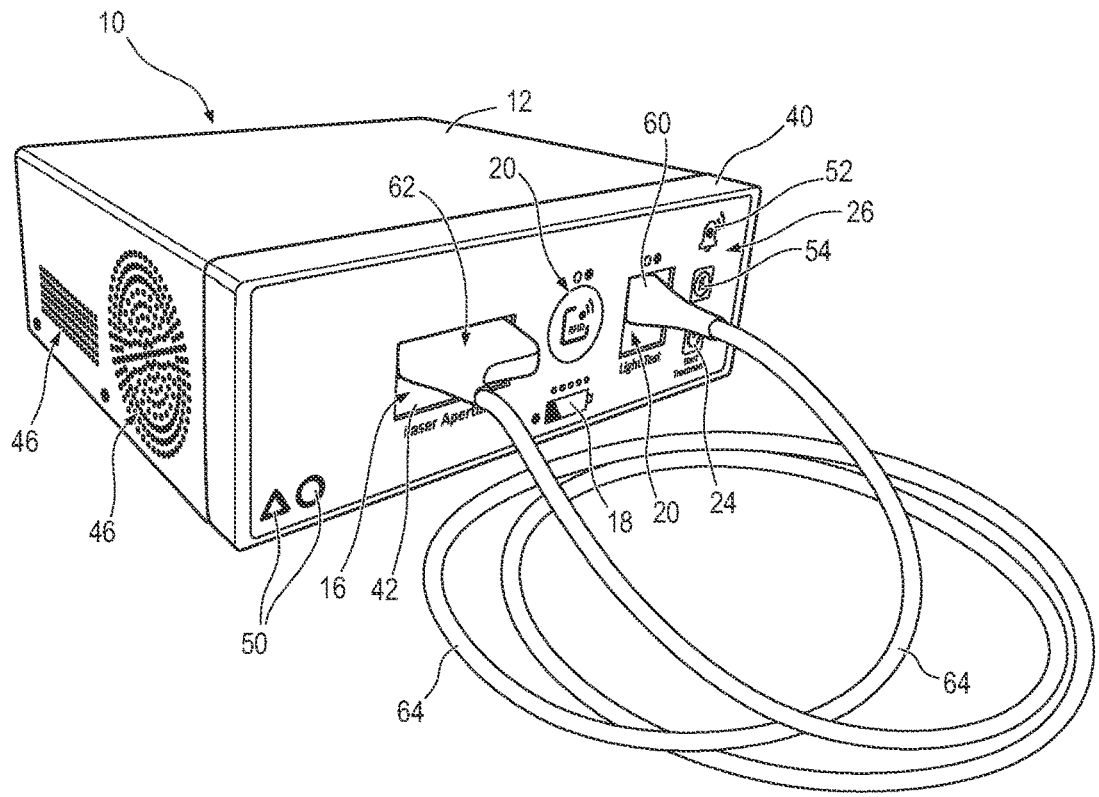
FIG. 5 is a perspective frontal view of the exemplary embodiment of the light engine box of FIG. 1 having an umbilical light transmission cable connected to the light engine box through the laser aperture, showing the umbilical light transmission cable in a light testing mode.

FIG. 5 is a perspective frontal view of the light engine box 12 of FIGS. 1 and 4 having the umbilical light transmission cable connected to the light engine box through the laser aperture, showing the umbilical light transmission cable 44 in a light testing mode by engagement through the light test aperture 22. The nature of the connection and the light testing mode will be referenced and described below.

Of particular interest to each of the contemplated embodiments of the present invention, the use of light (EMR) may have wavelengths ranging from above 380 nm and about 904 nm. Additionally, the intensity and power of the light emitted serves to inactivate infectious agents and/or to promote healing. A of radiant exposures covering 0.1 J/cm$^2$ to 5 kJ/cm$^2$ (or in some instances up to 10 kJ/cm$^2$), and a range of powers from 0.005 mW to 5 W (or in some instances up to 10 W), and power density range covering 1 mW/cm$^2$ and 2 W/cm$^2$ (or in some instances up to 5 W/cm$^2$) are of interest for these exemplary device assemblies and methods. These ranges of wavelengths, power densities, and radiant exposures have been shown to have either antimicrobial effects or positive biological effects on healing tissue. These positive biological effects include reduction of inflammatory cells, increased proliferation of fibroblasts, stimulation of collagen synthesis, angiogenesis inducement and granulation tissue formation.

For each exemplary embodiment described herein, each laser assembly 34, its delivery mechanism, and the delivery method for disinfecting/healing may be utilized and controlled manually or by a CPU 35 to provide an adjustable or predetermined duty cycle. If treatments begin immediately after sterile procedure has been initiated or in some instances, if treatments proceed during a sterile procedure, device-related infections may be prevented, inhibited, or eliminated. This includes device-related biofilm growth. For example, the EMR delivery system may provide one duty cycle for preventing device-related infections prior to beginning dialysis and another different duty cycle for during the dialysis process, or one duty cycle may be tailored for females and another different duty cycle may be tailored for males. With the use of the CPU 35 that is pre-programmed or programmable, many different types of duty cycles may be stored within the CPU's memory for recall and use when appropriate. Such different types of duty cycles may differ by different parameters such as wavelength, intensity, and duration having differing values within the ranges disclosed herein or by having different dosing technique parameters (for example, the HISD technique, discussed below, differs from a steady non-changing dose for a given time duration).

Additionally, although a wavelength in a range from 380 nm to 904 nm with a sufficient intensity will inactivate one or more infectious agents and/or enhance healthy cell growth, more precise wavelengths may have enhanced efficacy against certain infectious agents or for a desired healing purpose. It has been determined that sterilizing EMR of wavelengths including wavelengths centered about 400 nm, 405 nm, 415 nm, 430 nm, 440 nm, 455 m, 470 nm, 475 nm, 660 nm, and 808 nm have efficacy. A wavelength selected to promote healing and healthy cell growth may be selected from the group of wavelengths centered about 632 nm, 632.8 nm, 640 nm, 650 nm, 660 nm, 670 nm, 680 nm, 780 nm, 808 nm, 830 nm, and 904 nm.

Because dosing techniques may differ with different intended uses, the invention of this disclosure provides the versatility that may accommodate different uses and different dosing techniques, particularly when programmable into and controlled by an internal CPU 35. For example, if the intended use is to deliver EMR to sterilize an extension set or a coupling disposed outside of a patient's body the power of and exposure to the EMIR may be more aggressive than might be the case if the EMIR delivered is for preventing, inhibiting, or eliminating infectious agents within the patient's body a more moderate EMIR may be used. Additionally, if there is a time constraint that may be advantageous to the user/patient that may be met or optimized by a High Intensity-Short Duration (HISD) technique, for which the invention of this disclosure is particularly suitable, whereas a lower power administered over a longer period may also be administered using the invention of this disclosure.

The HISD technique can be effective in preventing, inhibiting, and eliminating particularly stubborn infectious agents. For example, a 35-minute treatment using two 1 W laser diodes may be administered up to a radiant exposure of 270 mW/cm$^2$ which equates to approximately 570 J/cm$^2$. This type of treatment may be used outside the patient's body before starting dialysis, while a less aggressive 4-hour treatment delivering EMR inside the patient's body may use the same light engine box 12. It is contemplated that 20-minute treatments that are slightly more aggressive than a 35-minute treatment may be used in some instances and will be very advantageous to dialysis patients, reducing total connect time with the dialysis system and adding in-home convenience and comfort.

In short, the invention of the present disclosure may provide an avenue for thousands of dialysis patients to receive competent and safe treatment at home for a fraction of the cost in time, money, comfort, and convenience of clinic and/or hospital administered dialysis. Of course, the invention of the present disclosure may be used in some clinic and hospital settings and is not limited to dialysis use.

Turning now to FIG. 1 with specific reference to the smart light engine system 10 and enclosed within and presented by the light engine box 12, the light engine box 12 is displayed as a substantially rectangular box with soft-rounded edges for comfortable handling and has venting features 46 to assist in the dissipation of heat that may be generated by the smart light engine system 10. The front panel 40 has the front panel overlay 14 connected thereto to present a user interface 48 making various features and connections available to a user/patient in the operation of the smart light engine system 10. The front panel overlay 14 may present to the user/patient warning icons 50, the laser aperture 16, the battery power indicator 18, the RFID feature 20 indicator, the light test aperture 22, the treatment on/off actuator 24, and alarm features 26.

Although the drawings and description herein are directed to a smart light engine system, of course, a light engine system that does not have any of the versatility features shown and discussed herein is also contemplated. For example, a laser assembly 34 may be factory preset to a particular wavelength and intensity that provides a duty cycle regulated by an on/off switch that determines duration of use.

The laser aperture 16 provides connection access of the proximal end of the umbilical light transmission cable 44 directly to the laser assembly 34 through the dust covers 42. The dust covers 42 inhibit handling and dust contamination of the connection environment between the umbilical light transmission cable 44 and the laser assembly 34 (shown in FIG. 3), thereby maximizing the efficiency of light (EMR) transmittal from the EMR source into the umbilical light transmission cable 44.

Best shown in FIG. 3 is a schematic depiction of a central processing unit (CPU) 35 that controls features provided by the smart light engine box such as those that are displayed on the front panel overlay 14; namely, for example, the battery power indicator 18, the RFID feature 20, the treatment on/off actuator 24, and the alarm features 26. The CPU 35 is connected to the power supply (battery and/or power outlet) and is pre-programmed and/or programmable. The operation of the CPU 35 to control the features disclosed herein is within the experience and knowledge of those skilled in the art once armed with the disclosures and teachings of this specification. Consequently, the specific circuitry and wiring is not shown so that the components of the EMR delivery system are not unnecessarily obscured.

The battery power indicator 18 may provide a visual indication to the user/patient of the status of the battery charge capability of the battery assembly 36. The battery assembly 36, best shown in FIG. 3, is provided to maintain operability of the smart light engine system 10 if power from an institutional power source (for example, a power outlet or a generator) is interrupted, lost, or unavailable. Hence, the battery assembly 36 may serve as a safety backup feature or a rechargeable battery may provide the principal power source with the battery power indicator 18 alerting the used when recharging is needed. The battery power indicator 18 arms the user/patient with power-related information and peace of mind that the smart light engine system 10 will properly operate through a complete treatment cycle, even if the power source is interrupted, lost, or unavailable for any reason.

The RFID feature 20 indicator is the interface used for monitoring and tracking use of a disposable component (to be referenced and described below) used to facilitate sterile connection of the umbilical light transmission cable 44 to a catheter such as, for example, a peritoneal dialysis catheter ("PD catheter") by the user/patient to prevent overuse of the disposable component. The RFID feature 20 has a RFID reader with a built-in antenna (not shown) that enables reading of RFID tags when placed near to the RFID feature 20 indicator. The CPU 35 communicates with the RFID reader to facilitate acknowledgement of the disposable component, monitor the use of the disposable component, and to activate an alert indicating that, for example, the disposable component is unable to complete another treatment before the predetermined useful life of the disposable component is exhausted.

The light test aperture 22 provides connection access of the distal end of the umbilical light transmission cable 44, through the dust covers 42, directly to the side port test module 38. The dust covers 42 inhibit handling and dust contamination of the connection environment between the umbilical light transmission cable 44 and the side port test module 38 (shown in FIG. 3), thereby providing the ability to test the light emanating from the umbilical light transmission cable 44 to verify that it is the desired EMR (wavelength and intensity) for the intended treatment and the ability to determine the health of the laser diode within the laser assembly 34 and any degradation in the light transmission of the umbilical light transmission cable 44, suggesting that either or both should be replaced. The CPU 35 communicates with the test module to facilitate testing of the EMR. The test module 38 sends test results to the CPU 35 to be analyzed against predetermined EMR parameters by comparing the tested EMR parameters to the desired EMR parameters so that the CPU 35 may determine the health of the laser diode within the laser assembly 34 and if there is any degradation in the light transmission of the umbilical light transmission cable 44 so that an alert may be activated indicating that, for example, the umbilical light transmission cable 44 has degraded and replacement is recommended or that the laser diode's useful life has been exhausted.

The treatment on/off actuator 24 may be a push button interface for actuation by the user/patient that, when actuated, initiates a pre-programmed or program selected duty cycle of EMR at prescribed wavelength(s), intensity(ies), and duration or interval(s) as stored in the CPU 35. The duty cycle may terminate automatically per the programing, or it may be terminated manually (e.g., by pushing the button interface) in the event of a justifiable need to terminate. Again, with the CPU 35 that is pre-programmed or programmable, many different types of duty cycles may be stored within the CPU's memory for recall and use when appropriate. Such different types of duty cycles may differ by different parameters such as wavelength, intensity, and duration having differing values within the ranges disclosed herein or by having different dosing technique parameters (for example, the HISD technique, discussed below, differs from a steady non-changing dose for a given time duration).

The alarm features 26 may comprise an alarm alert 52 that may be audible and/or visible and an alarm on/off actuator 54. The alarm alert 52 may make an audible sound (buzzing, ringing, speaking, and/or the like) and/or provide a visible alert (red/green light, flashing light, a read out, and/or the like). The alarm features 26 may provide feedback regarding various aspects of the treatment experience. For example, the alarm alert 52 may display a green light or play a "ready for use" message when the testing of the light emanating from the umbilical light transmission cable 44 indicates that the light is ready for use in the intended treatment; or, the alarm alert 52 may display a red light or play an error message when the testing of the light emanating from the umbilical light transmission cable 44 indicates that the light is defective or not ready for use in the intended treatment. The alarm on/off actuator 54 may be used to turn on the visible alert to test that it is operable, or it may be used to turn off an audible and/or visible alert that has been triggered to alert the user/patient. Additionally, the alarm features 26 may be used to raise the awareness of the user/patient to any operating aspects of the smart light engine system 10. For example, actuating the alarm on/off actuator 54 during treatment may trigger the alarm alert to audibly provide that time remaining in the treatment or some other operating aspect that is being monitored or tracked by the system 10 (for example, the amount of radiant exposure or the amount of time remaining for the present disposable to be used before replacement). Each of the alert features 26 discussed in this paragraph and throughout this disclosure may be controlled by the CPU 35 which is in communication with the alarm alerts 52 and various components that may trigger an alarm alert 52. Again, the design and operation of the CPU 35 to control the alarm features disclosed herein is within the experience and knowledge of those skilled in the art once armed with the disclosures and teachings of this specification.

The venting features 46 may comprise a series of holes as shown in FIG. 1 on one of the side panels, but such venting features may be slots or vents and may be located anywhere on the exterior of the light engine box 12 that will facilitate the dissipation of heat within the smart light engine system 10. For example, though some are not shown in the figures, the venting features 46 may be located on the back panel 28, the side panels, the top panel, or the bottom panel.

The warning icons 50 may be of any type that provide information to the user/patient. The smart light engine system 10 is a medical device that has operating components that may be harmful to persons or the environment if mishandled. The warning icons 50 may provide cautions, instructions, and/or use of product warnings directed at the user/patient. Exemplary warning icons 50 are shown generically as decals and labels on the front panel overlay 14 of FIG. 1 and the back panel 28 of FIG. 2.

The back panel 28 of the light engine box 12, best shown in FIG. 2, may present a second user interface 48 making various features and connections available to a user/patient in the operation of the smart light engine system 10. The back panel 28 may present to the user/patient, for example, warning icons 50, the on/off switch 30, and power ports 32. The on/off switch 30 may be the general on/off that controls the power being supplied to the light engine box 12 from an institutional source and/or the power being drawn from the battery assembly 36. In FIG. 2, the on/off switch 30 is located on the back panel 28, however, the on/off switch 30 may be located at any other conveniently accessible location on the exterior of the light engine box 12. For example, as shown in FIG. 4, or on either side panel or the top panel.

The power ports 32 may be of any type. Two such power ports 32 are shown in FIG. 2 as female adapters for receiving complementary power cords, by way of example, and to demonstrate that the system 10 may achieve more versatility of use by having multiple types of power ports 32. Of course, however, it is also contemplated that just a single power port 32 and/or a hard-wired power cord may be used to provide power to the light engine box 12.

Because FIG. 3 is an exploded view of an exemplary smart light engine system 10, various exemplary internal components are shown. As depicted, the exemplary smart light engine system 10 comprises the front panel overlay 14, the front panel 40 with dust covers 42, the laser assembly 34, the CPU 35, the battery assembly 36, the side port test module 38, a side port test adapter 56, a cable adapter 58, and various other components used in the alignment and assembly of components of the light engine box 12.

Although one laser assembly 34 is shown in FIG. 3, multiple laser assemblies 34 may be used to accomplish various capabilities by the light engine box 12. One laser assembly 34 may provide a certain wavelength at a certain intensity and a second identical laser assembly 34 may be configured to operate in tandem with the other laser assembly to provide EMR with the same wavelength and about double the intensity. For example, two NovaLum lasers (manufactured by Ushio America, Inc. of Cypress, California) operating at 1 W each at a given wavelength configured in tandem may produce EMR emitting at the given wavelength at about 2 W. Additionally, multiple laser assemblies 34 may provide the same wavelength and intensity to multiple umbilical light transmission cables 44 or differing wavelengths and intensities to a single or multiple umbilical light transmission cables 44.

The laser assembly 34 may have other operating capabilities. Such operating capabilities are known in the art but have not been used previously in an EMR delivery system as disclosed herein to disinfect and/or heal. For example, a laser assembly 34 may operate at a single wavelength for dedicated purpose or the wavelength may be adjustable and tunable from one wavelength to another, or the wavelength may be tunable only within a predetermined wavelength range (such as the blue light range or the range of 380 nm to 904 nm as disclosed herein). Also, a single laser assembly 34 operate to provide multiple wavelengths at the same time such as a disinfecting wavelength simultaneously with a different disinfecting wavelength and/or a healing wavelength.

One embodiment of the light engine box 12 has the laser assembly 34 disposed proximate or abutting the front panel 40 so that the umbilical light transmission cable 44 connects directly into the laser assembly 34 via a SMA adapter 58 (subminiature version A optical fiber connector) and may be connected directly into the side port test module 38 via a SMA adapter 58 as will be described below. The direct connection eliminates undesirable light bleed or loss so that the light produced by the laser assembly 34 and entering the umbilical light transmission cable 44 is identical or virtually identical to the light emanating from the distal end of the umbilical light transmission cable 44 for use in treatment dosing or to be tested by a photo diode when connected to the side port test module 38. Hence, any meaningful difference in the light being tested from the light produced accurately senses and measures the health of the laser diode in the laser assembly 34 and any degradation of the umbilical light transmission cable 44 over time as the umbilical light transmission cable 44 is repeatedly used during treatments and tested periodically before each treatment, as recommended. The user/patient may, with confidence, maximize the useful life of the umbilical light transmission cable 44 and know precisely when it should be replaced so not to compromise dosing treatments.

FIG. 4 and FIG. 5 show exemplary light engine boxes 12 in the "ready to use" mode and the "testing" mode, respectively. By connecting the umbilical light transmission cable 44 to the laser assembly 34 through the laser aperture 16 the EMR (light) is transmitted from the laser assembly 34 to a wide range of remote locations that facilitates use of the light engine system 10 within institutional (hospital, clinic, etc.) and home-use settings. The light engine system 10 enables a range of mobility during the sterilizing operation and/or during treatment, making the experience much more comfortable and efficacious for in-home treatments that heretofore have not been possible, thereby dramatically reducing catheter related infections (CRIs), medical costs and insurance costs while providing convenience and comfort to the patients receiving treatments.

Figure 6:
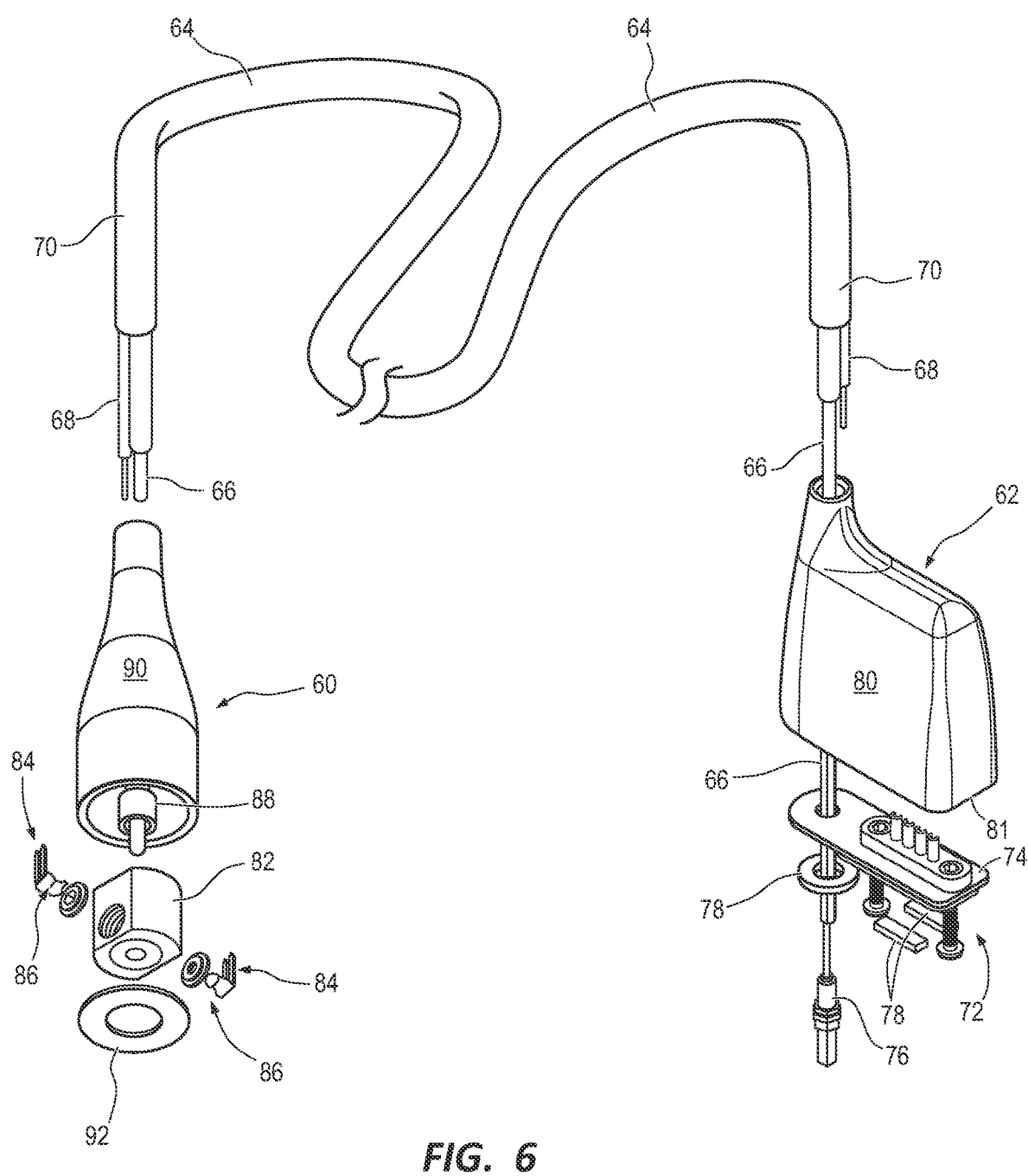
FIG. 6 is an exploded perspective view of an exemplary embodiment of an umbilical light transmission cable showing various components, including a distal connector and a proximal connector.
Figure 7:
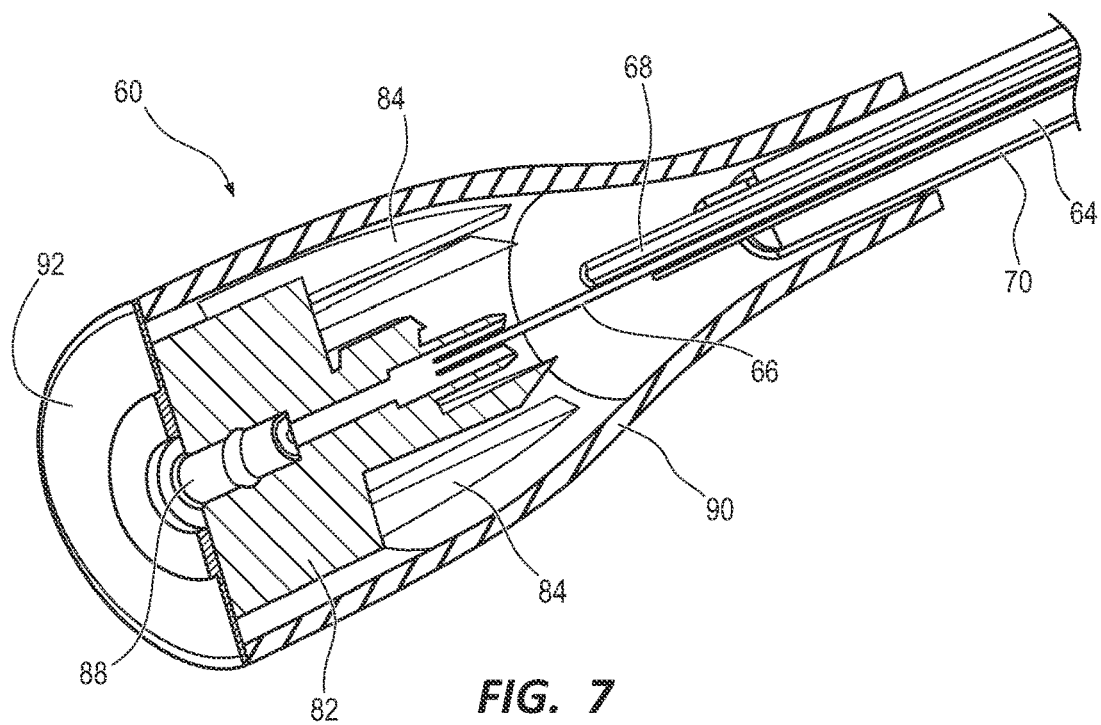
FIG. 7 is a perspective vertical section of the distal connector of the exemplary embodiment of the umbilical light transmission cable of FIG. 6.
Figure 8:
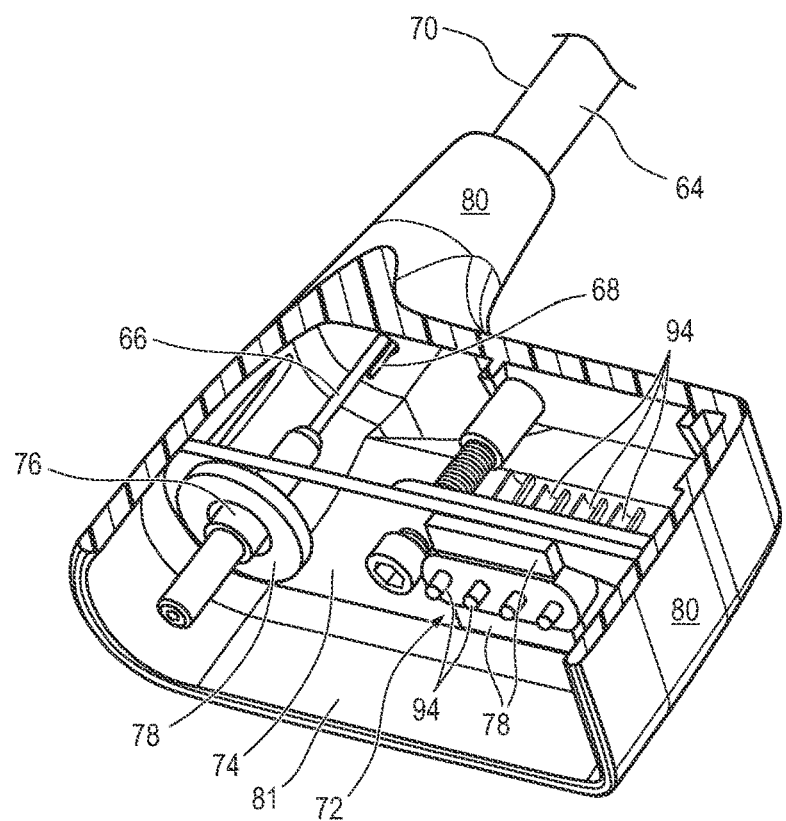
FIG. 8 is a perspective horizontal section of the proximal connector of the exemplary embodiment of the umbilical light transmission cable of FIG. 6.

FIGS. 6-8 are directed to the component parts and operation of an exemplary umbilical light transmission cable 44. The exemplary umbilical light transmission cable 44 depicted has several features in addition to the axial delivery of EMR. Of course, those skilled in the art, enabled by this disclosure, may make, and use umbilical light transmission cables 44 with more or lesser features or achieve axial delivery of the EMIR without departing from the scope and spirit of the invention disclosed in this application.

FIG. 6 is an exploded perspective view of an exemplary embodiment of an umbilical light transmission cable 44 showing various components, including a distal connector 60, a proximal connector 62 and a cable 64 therebetween. The cable 64 comprises fiber optics 66, wire(s) 68 and a cable sleeve 70. The proximal connector 62 comprises a first optical interlock 72 with an optical interlock connector 74, a proximal SMA 76, securement magnet(s) 78, and a proximal connector shell 80 with an extended forward edge 81 (best shown in FIG. 8 below). The distal connector 60 comprises a SMA adapter 82 having a second optical interlock 84 with press-in ball joint(s) 86, a distal SMA 88, a distal connector shell 90, and a front cover 92. These interlocking features provide safe and secure connections to prevent undesired disconnection that may permit randomly directed laser light, undesired light scattering, or insufficient light for disinfection.

The cable 64 of the umbilical light transmission cable 44 may be of any suitable length and be manufactured to various standard lengths suitable for differing uses. For example, the length of cable 64 for in-hospital used may be shorter than the cable 64 designed for in-home use where the patient is likely more mobile. The fiber optics 66 may be a single fiber or a bundle of fibers, as needed, and may have negligible or minimal attenuation to minimize or virtually eliminate light loss while axially propagating through the fiber optics 66. The wire(s) 68 may be transmission wire(s) used for the transmission of data or electricity the facilitate the smart features of the smart light engine system 10 or to provide downstream electrical power where needed.

FIG. 7 depicts a vertical section of the distal connector 60 of the umbilical light transmission cable of FIG. 6 fully assembled with the wire(s) 68 truncated so not to obstruct view of other internal components. The fiber optics 66 are shown securely connected and aligned with the distal SMA 88 nested securely within the SMA adapter 82 and locked into position by the second optical interlock 84 so that a proper connection and alignment is maintained, and light loss is minimized or eliminated at the connection juncture. These internal components are encased within the distal connector shell 90 and the front cover 92 to keep the interior components free of contaminants such as dust and moisture. As depicted, the distal connector 60 may be connected to the side port test module 38 or other downstream implements such as a disposable, a connector, or a catheter to facilitate the further transmission of EMR. Examples of such downstream implements will be described below.

FIG. 8 depicts a vertical section of the proximal connector 62 of the exemplary umbilical light transmission cable 44 of FIG. 6 fully assembled again with the wire(s) 68 truncated so not to obstruct view of other internal components. The proximal connector 62 has an extended forward edge 81 that engages and opens the dust cover 42 doors (that swing open inwardly) to protect the polished fiber optics 66. The fiber optics 66 are shown securely connected and aligned with the proximal SMA 76 securely positioned and locked into position by the first optical interlock 72 so that a proper connection and alignment is maintained, and light loss is minimized or eliminated at the connection juncture. The wire(s) 68 (though shown as truncated) may be attached to pins 94 to facilitate the transmittal of data and/or electrical power from the light engine box 12 to the umbilical light transmission cable 44 for further transmission downstream of the umbilical light transmission cable 44. The securement magnets 78 provide magnetic resistance to dislodging the connection between the light engine box 12 and the proximal connector 62 so that alignment and connection is not compromised inadvertently. To disengage the proximal connector from the light engine box 12 requires a pulling force that overcomes both frictional and magnetic resistance. These internal components are encased within the proximal connector shell 80 and the optical interlock connector 74 to keep the interior components free of contaminants such as dust and moisture.

FIGS. 9-11D are directed to the component parts and operation of an exemplary fiber optic disposable 96 that is notable for its ease of use while maintaining system sterility. The exemplary fiber optic disposable 96 has an elongate structure comprising an optical fiber 98 enclosed within a collapsible/retractable sleeve 100 and disposed between a proximal end 102 and a distal end 104. The fiber optic disposable 96 may be constructed to various overall lengths to accommodate the desired length of optical fiber 98 to be advanced into sterilizing position within a tubular structure such as a catheter, extension line tube, and the like.

Figure 9:
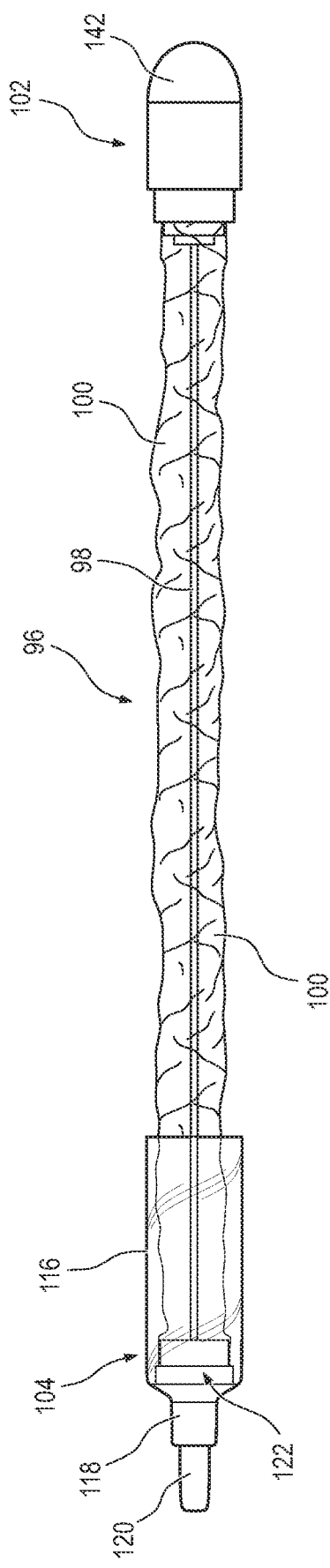
FIG. 9 is a plan view of an exemplary embodiment of a fiber optic disposable.

FIG. 9 depicts the exemplary fiber optic disposable 96 in its unused or fully retraced mode detached from connection to the umbilical light transmission cable 44 and any downstream connection. As depicted, the optical fiber 98 is enclosed within the collapsible/retractable sleeve 100 that provides a sterile environment inside the collapsible/retractable sleeve 100 between the proximal end 102 and the distal end 104 that serve to seal the ends of the collapsible/retractable sleeve 100 to encapsulate and preserve the sterile environment. In an exemplary embodiment of the fiber optic disposable 96, the collapsible/retractable sleeve 100 may be formed of a flexible, gas-impermeable polyethylene (PE) plastic and/or the optical fiber 98 may be plastic.

Figure 10:
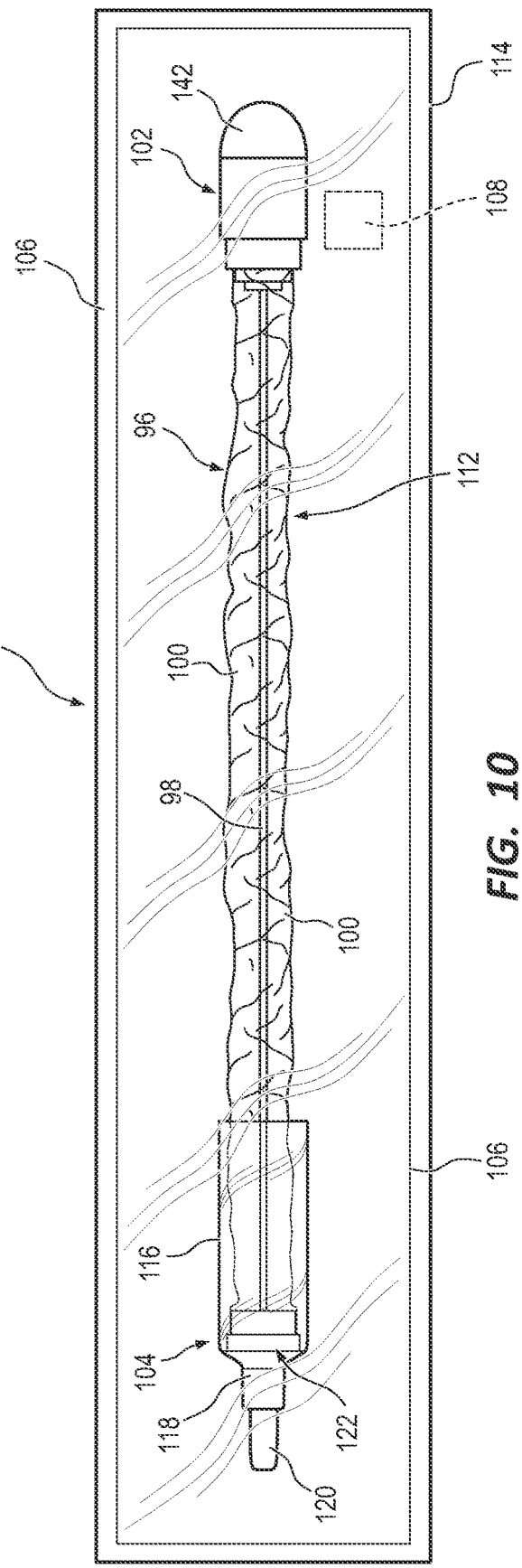
FIG. 10 is a plan view of an exemplary embodiment of packaging for the fiber optic disposable of FIG. 9, showing the fiber optic disposable disposed within the packaging.

FIG. 10 is a plan view of an exemplary embodiment of packaging 106 for the fiber optic disposable 96 of FIG. 9, showing the fiber optic disposable 96 disposed within the packaging and an RFID adhesive tag 108 (shown in phantom lines) attached to the exterior surface of the packaging 106. The packaging 106 may be of any suitable type that maintains the sterility of the fiber optic disposable during transport and storage. The exemplary packaging 106 depicted is face seal blister packaging 110 comprising a see-through blister face 112 and an opaque backing 114. FIGS. 9 and 10, show the fiber optic disposable in its retracted mode.

By placing the RFID adhesive tag 108 within readable proximity to the RFID feature 20 indicator on the front panel overlay 14 of the light engine box 12 the fiber optic disposable 96 within the packaging 106 having the RFID adhesive tag 108 may be registered with the smart light engine system 10 and initiate monitoring use of that specific fiber optic disposable 96. Such monitoring helps prevent using fiber optic disposables 96 that compromised by fluid over fiber degradation of the optical fiber 98. Each fiber optic disposable 96 may have a predetermined useful life for safe and effective use; therefore, tracking the age of the optical fiber 98 and the accumulated time of use may prevent an undesirable use of an optical fiber 98 that has been time/use compromised. For example, depending on the nature of the use, the useful life may be determined to be a week to ten days and/or ten uses and/or no more than twenty-five total hours (similarly to recommended oil changes in a vehicle being at three months or 3,000 miles intervals). The monitoring and tracking performed by the smart light engine system 10 may determine how long, how many uses, and/or how much total use duration is acceptable for the proper use of the fiber optic disposable and activate notice to the user/patient when the in-use fiber optic disposable 96 has expired and needs to be replaced with a fresh fiber optic disposable 96. The activated notice may take any suitable form; for example, the alarm alert 52 may provide audible and/or visual alert(s), the treatment on/off actuator may be disabled, and/or the laser assembly 34 may be disabled until a fresh replacement fiber optic disposable 96 is registered via the scanning of its RFID adhesive tag 108 at the RFID feature 20 of the light engine box 12.

These registering, monitoring, and replacement noticing capabilities are "smart" features of the smart light engine system 10. Any given light engine box 12 may not have any or each of these "smart" features but may have one or more other "smart" features (such as the "smart" features that determines and provides notice of a tired laser diode and/or degradation of the umbilical light transmission cable 44 described above). In fact, a light engine box 12 is not required to have any of the smart features disclosed herein so long as it capably delivers EMR for use to prevent, reduce, or eliminate infectious agents in a catheter or in a catheter extension or catheter connections. However, the efficiency and efficacy of preventing, reducing, or eliminating infectious agents is enhanced by having one or more of the "smart" features operating within the smart light engine system 10.

FIGS. 11-11D best show the component parts and operation of the fiber optic disposable 96. FIG. 11 is an exploded view of the fiber optic disposable 96 of FIG. 9 showing various component parts and the relative disposition of each component part. The proximal end 102 comprises a barrel 116 with a female luer adapter 118 that serves as a coupling adapter (in FIG. 9, a male luer plug 120 plugs the female luer adapter 118 for transport and storage), a check valve 122, and a capture ring 124. The check valve 122 captures the proximal end of the collapsible/retractable sleeve 100 and secures it against the inside wall of the barrel 116. The check valve 122 (also depicted in FIG. 11A in an exploded view) further comprises a check valve body 126, a check valve disk 128, a check valve cap 130, and a central bore 132 aligned through each component of the check valve 120 and is the bore through which the optical fiber 98 passes when advanced. As the optical fiber 98 is advanced the collapsible/retractable sleeve 100 is collapsed to nest within the barrel 116 placing the fiber optic disposable 96 into its fiber-advanced, collapsed mode. The check valve 122 permits the sterile environment inside the collapsible/retractable sleeve 100 between the proximal end 102 and the distal end 104 to move/escape through the check valve 122 as the fiber optic disposable 96 is advanced from its retracted mode to its collapsed mode (which also is a fiber-advanced mode).

The distal end 104 (also shown in FIGS. 11B-11D) further comprises a barrel plug 134 with a barrel plug cap 136, a ferrule 138, a magnetic washer 140, a ferrule cap 142 and an optical fiber receiving bore 144 centrally aligned through each component of the barrel plug 134. The ferrule cap surrounds and protects the ferrule 138 during transport and storage. The barrel plug 134 seats into and seals the barrel 116 capturing the collapsible/retractable sleeve 100 snugly within the interior of the barrel 116. The proximal end of the collapsible/retractable sleeve 100 is secured in air-tight fashion about the barrel plug cap 136 to maintain the sterility of the interior of the collapsible/retractable sleeve 100. The optical fiber 98 has a reinforced end 146 that is disposed within and through the optical fiber receiving bore 144 for aligned connection to the distal connector 60 of the umbilical light transmission cable 44. FIG. 11B is a perspective view of the fully assembled distal end 104 ready for connection to the distal connector 60 of the umbilical light transmission cable 44 while FIG. 11C is an exploded perspective view of the distal end 104 detached from the collapsible/retractable sleeve 100 and the ferrule 138 and magnetic washer 140 exploded from the barrel plug 134. FIG. 11D is a perspective end view of the ferrule cap 142 engaged to surround and protect the ferrule 138 during transport and storage.

Figure 12:
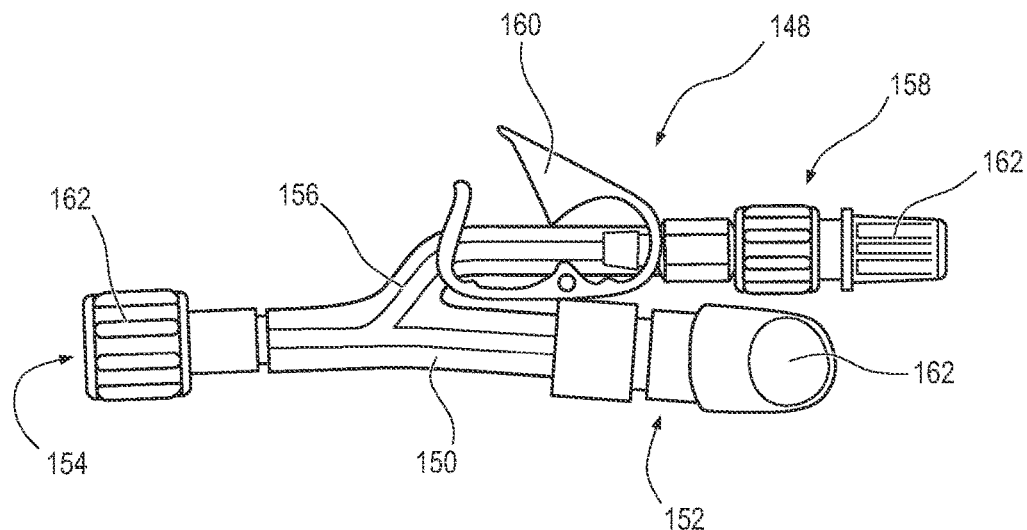
FIG. 12 is a plan view of an exemplary fiber optic introducer showing port connectors for connecting to an extension set, the distal connector via a fiber optic disposable, and a PD catheter, respectively.

FIG. 12 is a plan view of an exemplary fiber optic introducer 148 as it would appear during transport or storage with protective caps sealing each accessible port. The fiber optic introducer 148 shown is particularly suitable for use with a dialysis catheter having an extension set disposed between the dialysis catheter and a dialysate source or waste receptacle. As depicted, the exemplary fiber optic introducer 148 is a Y-connector having a main line 150 between an entry port 152 and an exit port 154 and a branching line 156 between the main line 150 and a side port 158. Also depicted are various accessories for the fiber optic introducer 148; namely, a clamp 160 for selectively closing and opening the branching line 156 and differing types of sealing caps 162 for sealing the entry port 152, exit port 154, and side port 158. Generally, Y-connectors are well known, although the depicted exemplary fiber optic introducer 148 is particularly suitable for use with a dialysis catheter. Consequently, the types of connections at the ports may differ from other Y-connectors to accommodate connections to an extension set, a dialysis catheter, and umbilical light transmission cable 44 (as shown in FIG. 13).

Although the depicted exemplary fiber optic introducer 148 is particularly suitable for use with a dialysis catheter, it should be understood the scope of the invention disclosed herein is not to be limited to use with a dialysis catheter. Rather, use of the invention with a dialysis catheter is intended as an example of one of many uses contemplated and applicant has selected to describe use with a dialysis catheter as representative and informative regarding other uses contemplated. Those skilled in the art, enabled by this disclosure, could readily modify the configuration of the exemplary fiber optic introducer 148 to accommodate different uses of the invention without departing from the intended scope and spirit of the invention.

Figure 13:
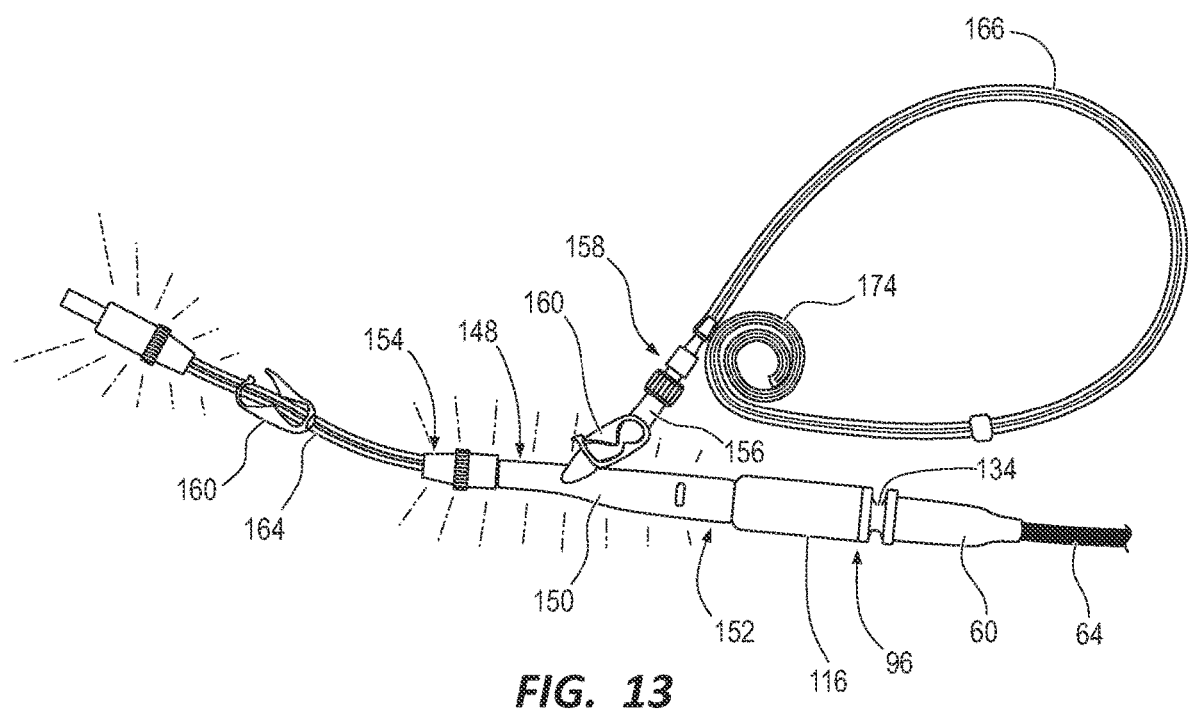
FIG. 13 is a plan view of an assembly of the exemplary fiber optic introducer, the extension set, the distal connector, the fiber optic disposable, and the PD catheter, respectively, showing light emission within the extension set, the fiber optic introducer, and the fiber optic disposable.

FIG. 13 depicts a representative use of the fiber optic introducer 148 in a representative peritoneal dialysis (PD) catheter environment. The fiber optic introducer 148 is shown connected to an extension set 164, a single-cuff PD catheter 166 and an umbilical light transmission cable 44 via a fully collapsed fiber optic disposable 96 (i.e., in its fiber-advanced, collapsed mode) with the fiber optic 98 advanced through the fiber optic introducer 148 into the tubular extension set 164. As depicted, the fiber optic introducer 148 facilitates the flow of fluids such as fresh dialysate and/or waste dialysate and the delivery of EMR for radial emission. With the depicted configuration, the optical fiber 98 has been advanced into and through the main line 150 of the fiber optic introducer 148 and into the extension set 164 (a tubular extension of the PD catheter 166 that is located outside of a patient's body) by advancing the optical fiber 98 and collapsing the collapsible/retractable sleeve 100 (not shown) into the barrel 116 of the fiber optic disposable 96 and into the fiber-advanced, collapsed mode. As extended, the optical fiber 98 is positioned to deliver and emit radially sterilizing EMR into, on, and around the fiber optic introducer 148 (having a tubular structure portion) and the extension set 164 (as depicted in an exemplary fashion by rays extending radially therefrom). In this fashion, the fiber optic introducer 148 and the extension set 164 may be sterilized before dialysis treatment is initiated to prevent infection agents from populating. However, if desired, the radial emission of sterilizing EMR may also be delivered and emitted when dialysate (fresh or waste) is present within the fiber optic introducer 148 and/or the extension set 164.

Figure 14A:
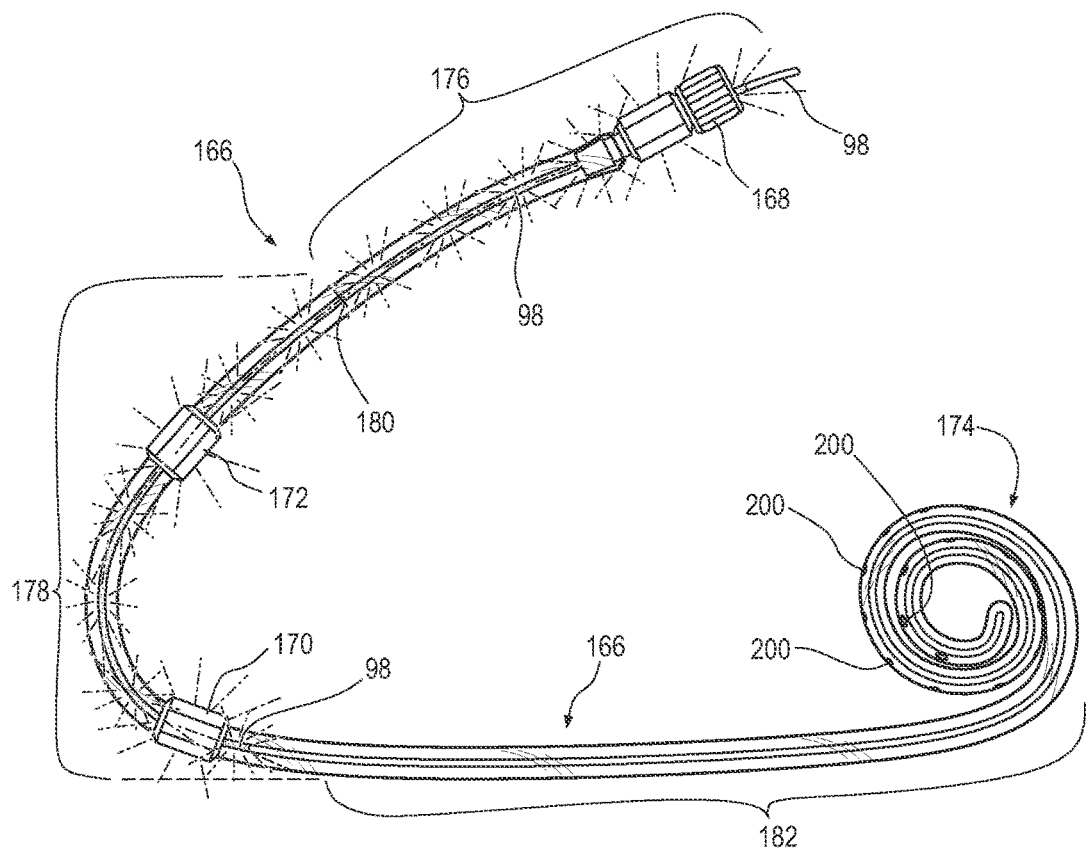
FIGS. 14A-C is a series of perspective views of an exemplary two-cuff peritoneal dialysis catheter illustrating exemplary radial EMR emissions.
Figure 14B:
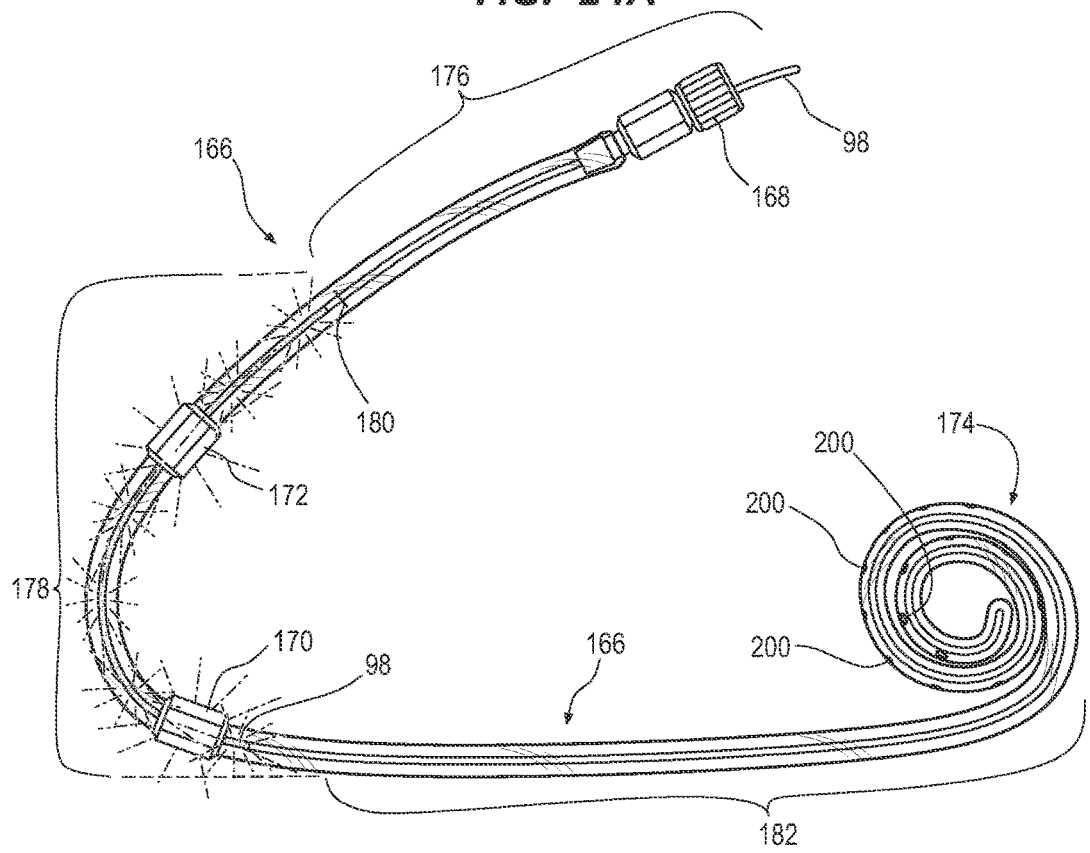
Figure 14C:
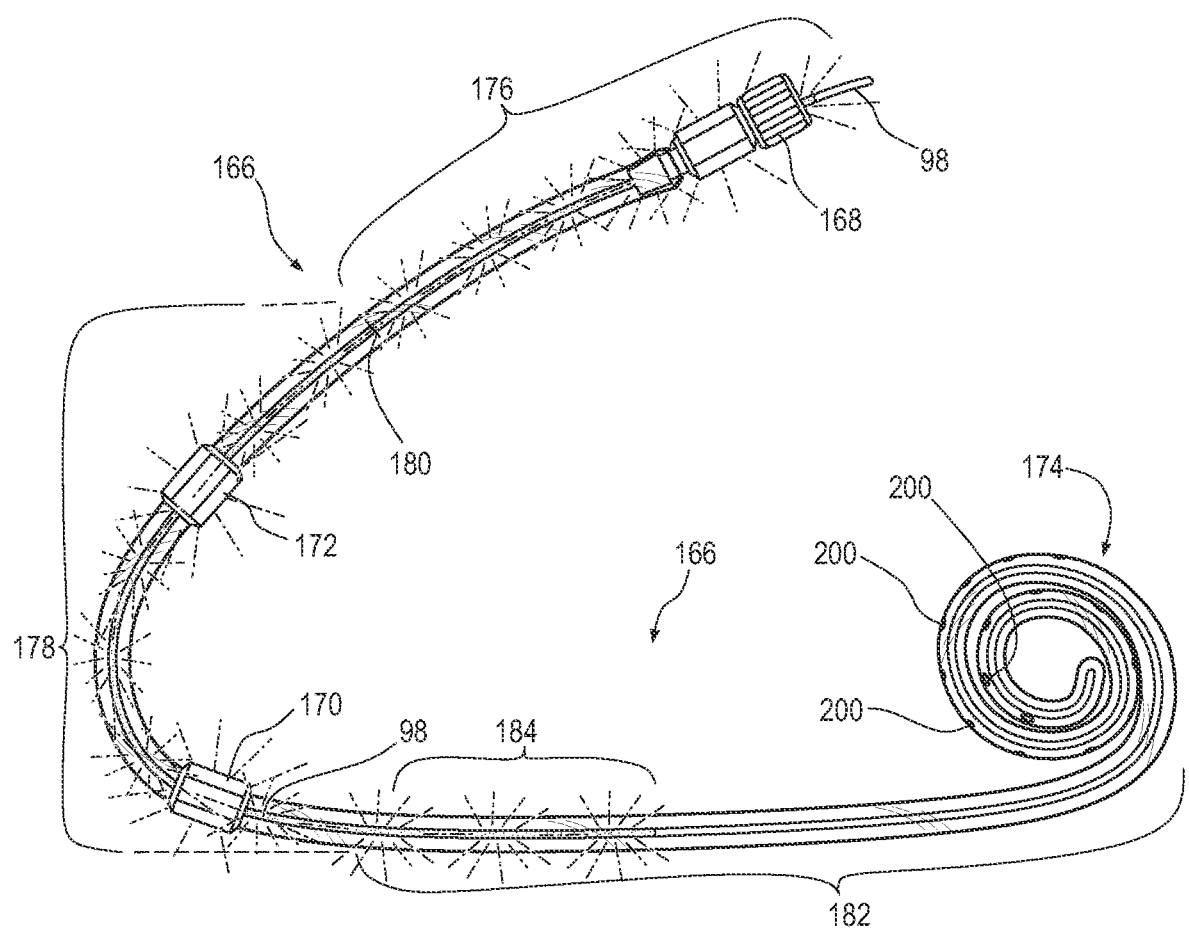

The collection of FIGS. 14A-C is a series of perspective views of an exemplary PD catheter 166 illustrating exemplary radial EMR emissions. Although both peritoneal dialysis and hemodialysis require access to a patient's body via some type of dialysis access (in this case a PD catheter 166), peritoneal dialysis has several advantages over hemodialysis including quality of life due to its ability to provide better patient mobility and independence, the simplicity of the dialysis access, the simplicity of use, as well as the clinical advantages of maintaining residual renal function and lower mortality in the first years after starting peritoneal dialysis. A disadvantage of peritoneal dialysis is the risk of peritonitis. Peritonitis is often the result of contamination with skin bacteria, but it may also be due to the retrograde migration of microbes on the catheter. Systemic or intra-peritoneal antibiotics may be administered, and the exchange volumes may be decreased. Although PD catheter-related peritonitis may resolve with proper antibiotic therapy, delivery of EMR using both controlled relative intensity and treatment region specific dosing utilized alternatively, simultaneously, or alternately may prove to be more effective in preventing and assisting in the treatment of peritonitis. If the infection persists, catheter removal and use of hemodialysis for 4-6 weeks may be required to resolve the peritonitis. Because there is a strong association between exit-site infections and subsequent peritonitis, early, preventative delivery followed by maintenance delivery of EMR as described herein may prevent, inhibit. or eliminate exit-site infections that may lead to peritonitis.

Peritoneal refers to the lining that surrounds the organs in a patient's abdomen. That lining is called the peritoneal membrane. It forms a space called the peritoneal cavity that can hold fluid. With peritoneal dialysis, a long-term indwelling or permanent catheter is inserted through the lining into the space around the patient's organs. Dialysis solution (also known as dialysate) is delivered through the catheter into that space. The peritoneal lining contains many blood vessels. The dialysate draws extra fluid, chemicals, waste out of those blood vessels and through the lining. The lining acts as a filter. The dialysate is left in place for several hours while dialysis occurs. Then the old, waste-laden solution (also known as waste dialysate) is allowed to drain out through the catheter for disposal. Fresh, clean solution (dialysate) is immediately delivered in, filling in the space again. This process of exchanging waste dialysate with fresh dialysate is called an exchange.

The two-cuff PD catheter 166 shown in FIGS. 14A-C comprises a connector hub 168, a peritoneal cuff 170, a subcutaneous cuff 172, and a coiled Tenckhoff 174. This exemplary PD catheter 166 has three regions, an external region 176, a tunneled region 178 (extending from the exit site location 180 to just inside the peritoneal membrane), and an intra-peritoneal region 182. When the two-cuff PD catheter 166 is placed within the patient, the external region 1768 protrudes from the body of the patient at the exit site location 180 and is visible, the tunneled region 178 is tunneled through the subcutaneous tissue, the rectus muscle, and the peritoneal membrane, while the intra-peritoneal region 182 is disposed within the peritoneal cavity. It should be understood the exit site is the region where external region 176 protrudes from the patient's body and is depicted as an exit site location 180 on the PD catheter 166 (in FIGS. 14A-C) when the PD catheter 166 is positioned for dialysis. An optical fiber 98 is shown as disposed within the lumen of the PD dialysis catheter 166 extending just beyond the peritoneal cuff 170.

FIG. 14A depicts the exemplary two-cuff PD catheter 166 showing an exemplary radial emission of EMR extending from and including the connector hub 168 to a point proximate to and downstream from the peritoneal cuff 170 inside of the peritoneal membrane (including radial EMR emission within the external region 176, and the tunneled region 178).

FIG. 14B depicts the exemplary two-cuff PD catheter 166 showing the radial emission of EMR between the exit site location 180 upstream of the subcutaneous cuff 172 and a point downstream of the peritoneal cuff 170 inside of the peritoneal membrane (radial EMR emission within the tunneled region 178).

FIG. 14C depicts the exemplary two-cuff PD catheter 166 showing the radial emission of EMR between the connector hub 168 and a point downstream of the peritoneal cuff 170 and extending into a peritoneal dialysis solution region 184 during dialysis (including radial EMR emission within the external region 176, the tunneled region 178, and the intra-peritoneal region 182).

Figure 15A:
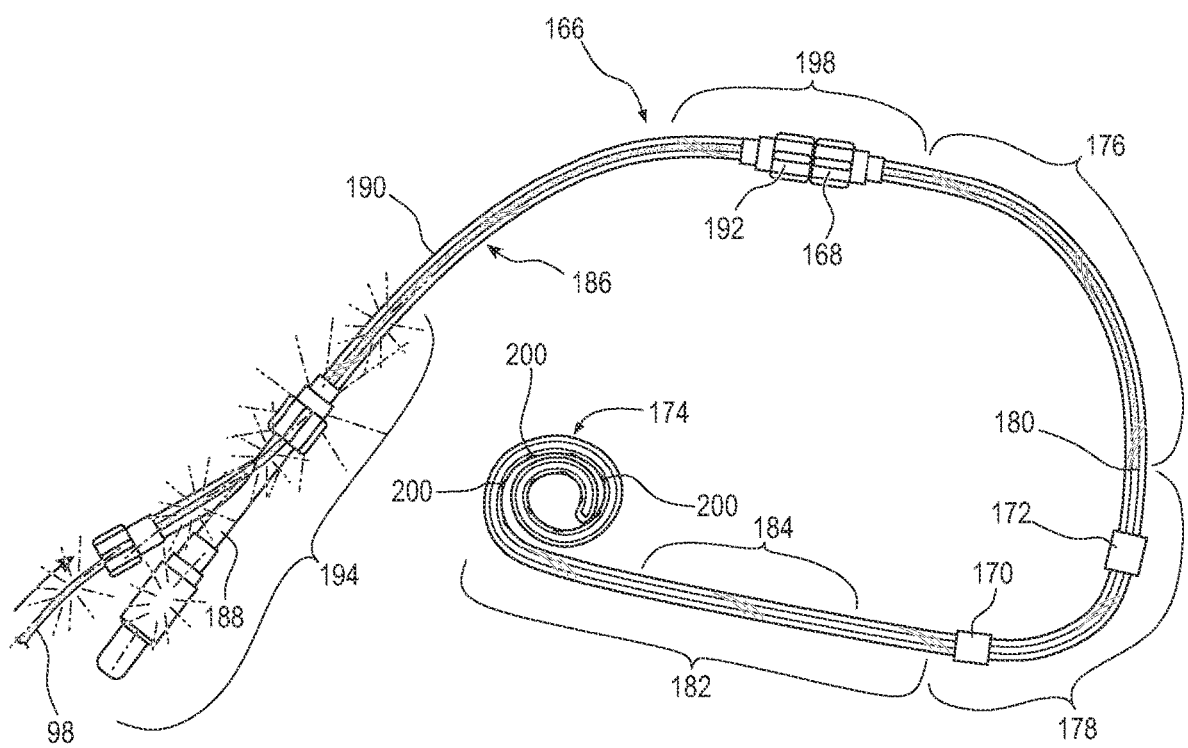
FIG. 15A is an elevation view of an exemplary two-cuff peritoneal dialysis catheter with an extension set interface showing radial EMR emission in the Y-site/transfer region only.

FIG. 15A depicts an exemplary extended PD catheter assembly 186 comprising a Y-port adapter 188, extension line tubing 190 (an exemplary tubular structure), and a connecting luer 192. Radial EMR emission is shown only in a Y-site/transfer region 194. In this configuration, the Y-port adapter 188 differs from the fiber optic introducer 148 in that the optical fiber 98 may be introduced into and through the branching line 156, into and through the extension line tubing 190, and into the PD catheter 166. The extent to which the optical fiber 98 extends into the extended PD catheter assembly 186 is determined by the length of the optical fiber 98. For example, for the configuration and the radial emission shown in FIG. 15A, the optical fiber 98 need only have an overall length that extends just beyond the Y-port adapter 188 when fully inserted.

Figure 15B:
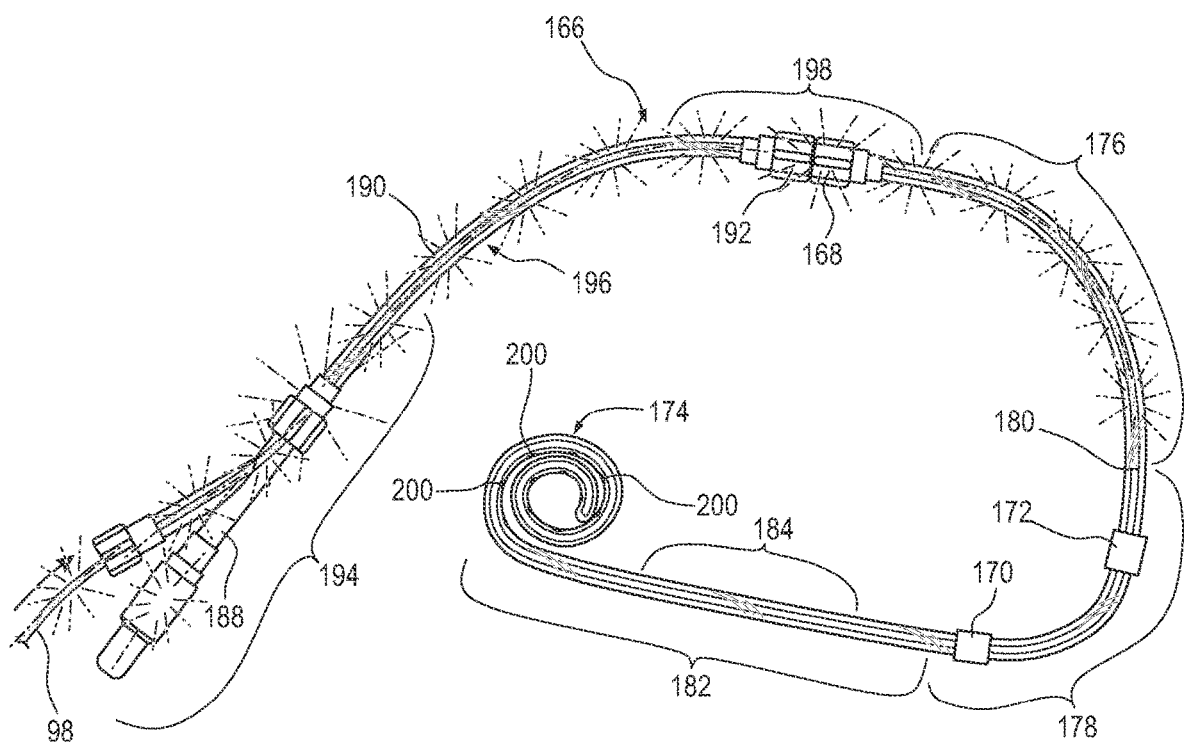
FIG. 15B is an elevation view of the two-cuff peritoneal dialysis catheter 10 connected to the extension set interface, showing radial EMR emission only exterior to the patient's body.

FIG. 15B depicts the exemplary extended PD catheter assembly 186 of FIG. 15A showing radial EMR emission only exterior to the patient's body within the Y-site/transfer region 194, within an extension set region 196, within a connection hub region 198, and within the external region 176. Additionally, for the configuration and the radial emission shown in FIG. 15B, the optical fiber 98 need only have an overall length that extends just short of the exit site location 180 when fully inserted.

Figure 15C:
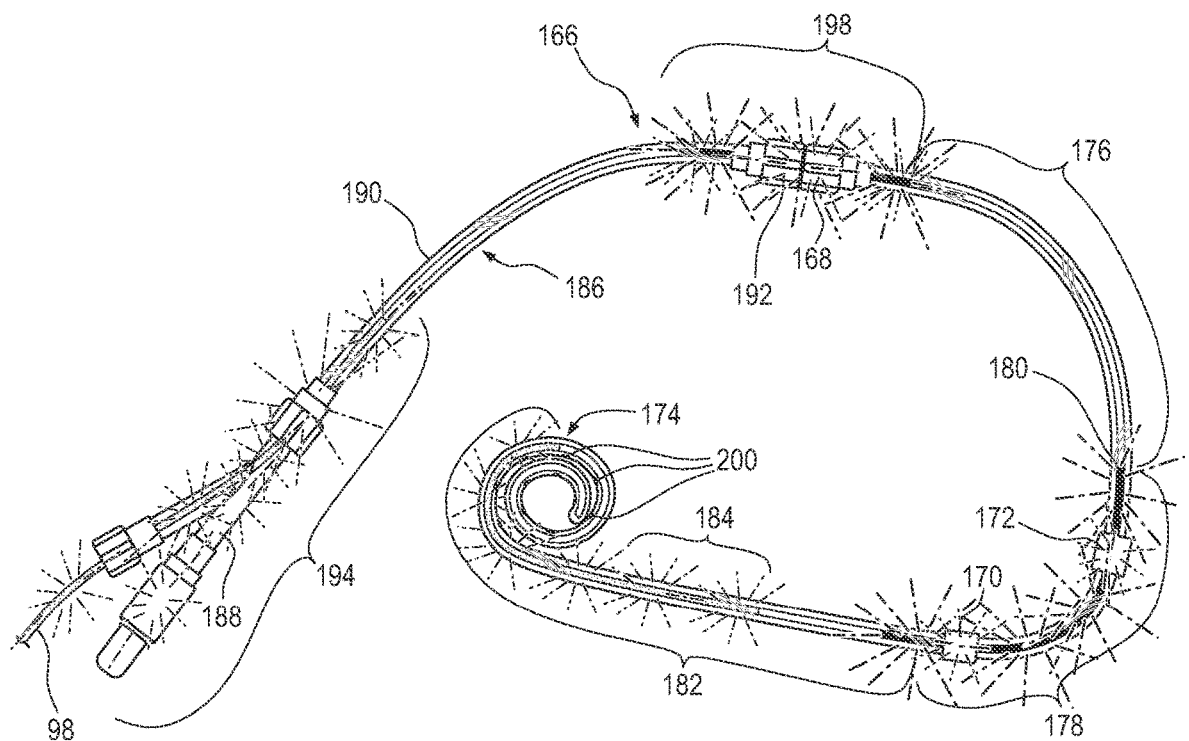
FIG. 15C is an elevation view of another exemplary two-cuff peritoneal dialysis catheter with an extension set interface showing radial EMR emission in the Y-site/transfer region, a connector hub region, a tunneled segment, and within the peritoneal dialysis solution region.

FIG. 15C depicts the exemplary extended PD catheter assembly 186 of FIG. 15A showing radial EMR emission along the full length of the at distinct regions: namely, within the Y-site/transfer region 194, the connection hub region 198, the tunneled region 178, and the intra-peritoneal region 182. This exemplary embodiment provides radial EMR emission in exterior regions susceptible to contamination-caused infections; namely, the Y-site/transfer region 194 and the connection hub region 198 simultaneously with radial EMR emission inside the patient's body. For the configuration and the radial emission shown in FIG. 15B, the optical fiber 98 has an overall length that extends through the extended PD catheter assembly 186 into the coiled Tenckhoff 174.

Radial EMR emission at distinct regions may be accomplished by emitting the EMR from multiple distinct radial emission portions along the optical fiber 98 as disclosed and described in the Parent Application.

Figure 15D:
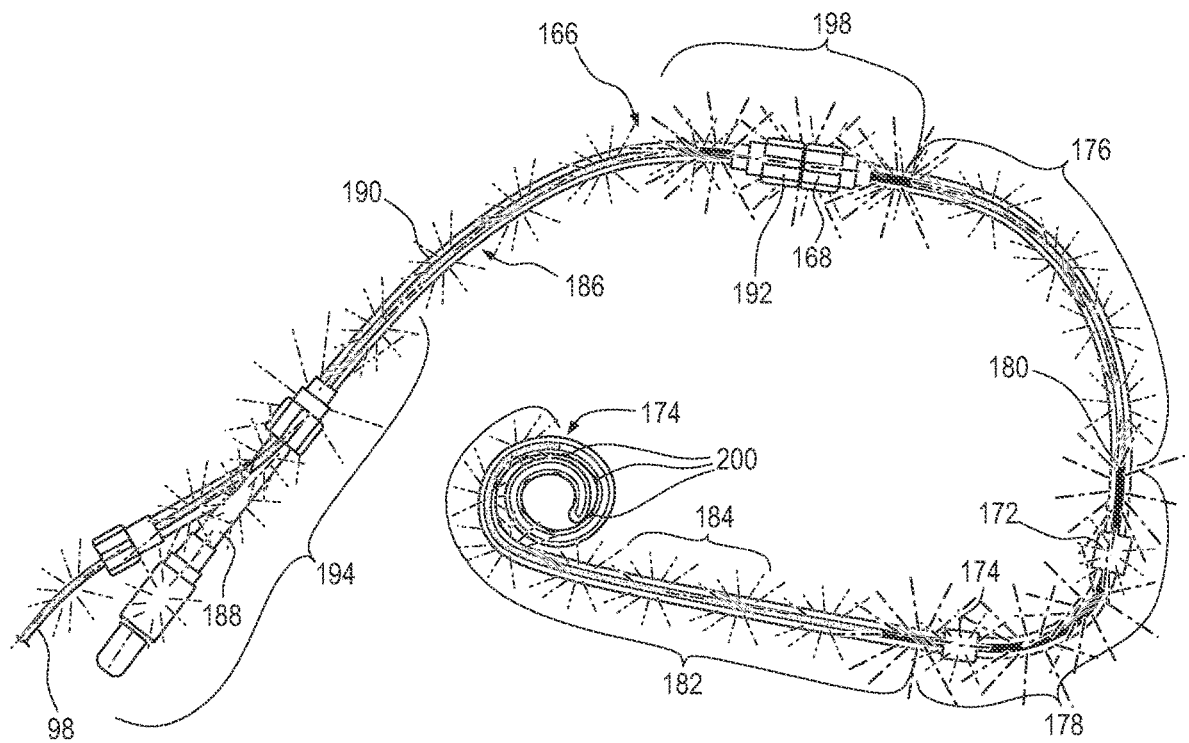
FIG. 15D is an elevation view of still another exemplary two-cuff peritoneal dialysis catheter with an extension set interface showing radial EMR emission in the Y-site/transfer region, a connector hub region, a tunneled segment, and within the peritoneal dialysis solution region extending into the coiled Tenckhoff.

Similarly, FIG. 15D depicts the exemplary extended PD catheter assembly 186 of FIG. 15A, however, this configuration shows radial EMR emission along the full length of the extended PD catheter assembly 186 to a point within the coiled Tenckhoff 174. This exemplary embodiment demonstrates that radial EMR emission may be delivered over the full extent of the extended PD catheter assembly 186, including exterior regions susceptible to contamination-caused infections and regions within the patient's body. In combination with the other figures, FIG. 15D demonstrates that any combination of regions along the length of the extended PD catheter assembly 186 may have radially emitted EMR on or off as desired to employ controlled relative intensity and/or treatment region specific application of the therapeutic doses.

Also, by extending the optical fiber 98 into the coiled Tenckhoff 174 as shown in FIG. 15D, the optical fiber 98 may prevent occlusion of holes 200 and/or tissue adhesion to the coiled Tenckhoff 174. To avoid uncoiling the coiled Tenckhoff 174, a smaller diameter optical fiber 98 fiber may be required (at least in the region of the optical fiber 98 that extends into the coiled Tenckhoff 174).

Figure 16A:
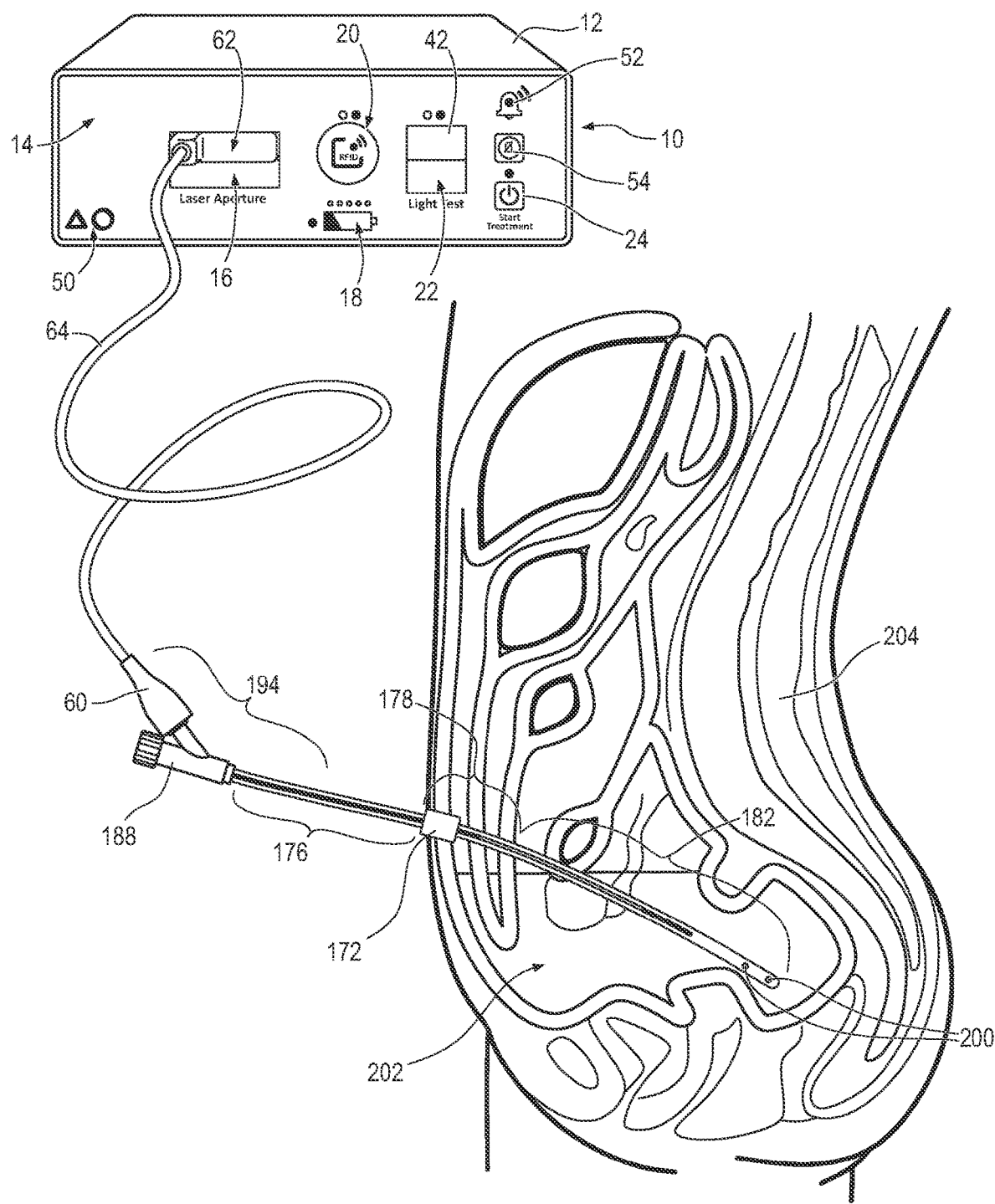
FIG. 16A is a schematic view of an exemplary embodiment of a single-cuff peritoneal dialysis catheter as connected to a light engine box via an umbilical light transmission cable and as inserted within a female patient's body.

FIG. 16A is a schematic view of another exemplary embodiment of a PD catheter 166 as inserted into peritoneal dialysis solution 202 within a female patient's body 204. This exemplary embodiment demonstrates a single-cuff PD catheter 166 connected to a light engine box 12 via an umbilical light transmission cable 44 and a Y-port adapter 188. No radial EMR emission rays are shown because the light engine box 12 is turned off.

Figure 16B:
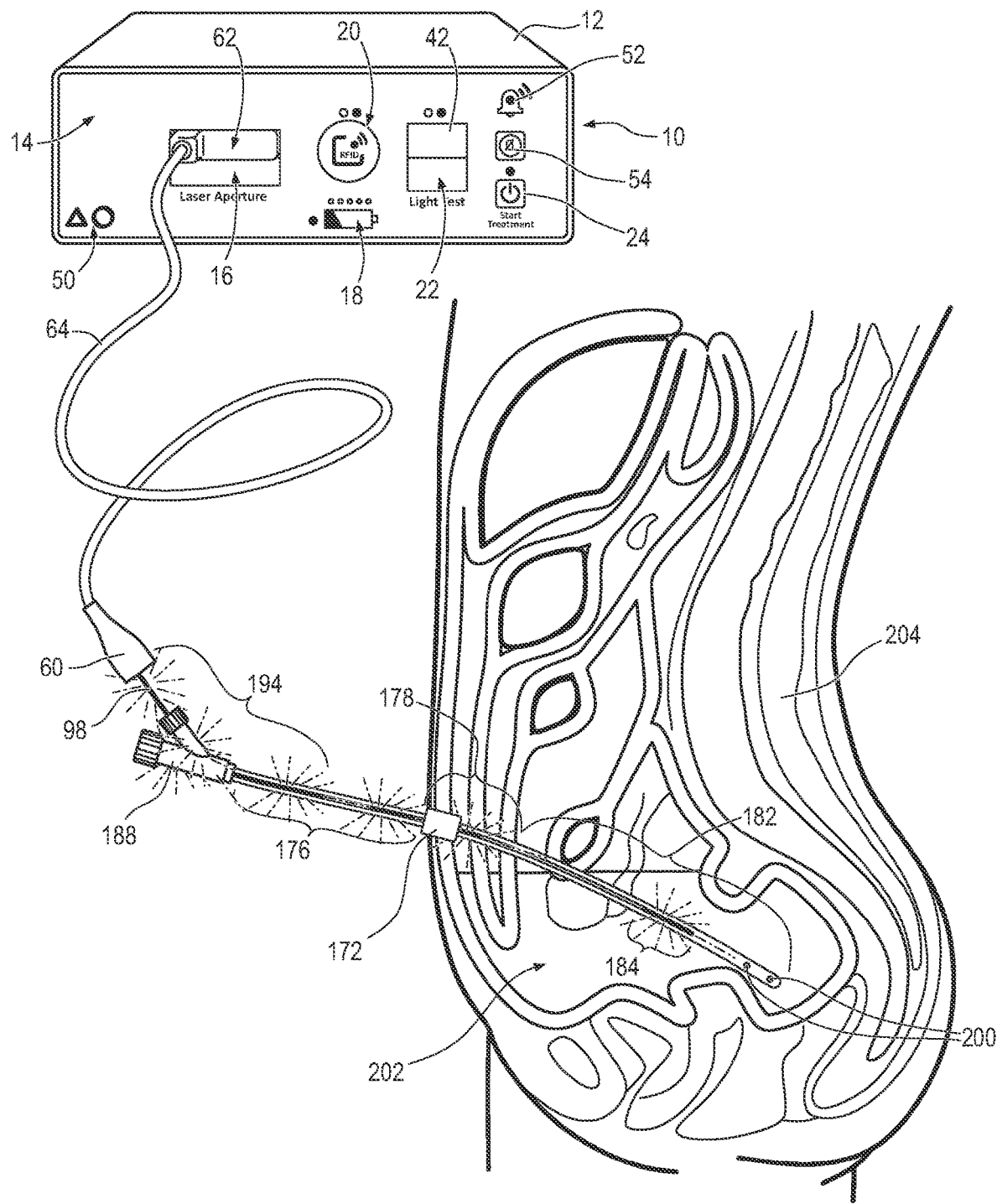
FIG. 16B is a schematic view of another exemplary embodiment of a single-cuff peritoneal dialysis catheter as connected to a light engine box via an umbilical light transmission cable and as inserted within a female patient's body showing radial EMR emission received from a point downstream of the EMR source to just downstream of the peritoneal cuff and within the peritoneal dialysis solution region.

FIG. 16B depicts the exemplary single-cuff PD catheter 166 as inserted within a female patient's body 204. This exemplary embodiment shows that the light engine box 12 has been turned on to provide radial EMR emission downstream of the light engine box 12 and the attached umbilical light transmission cable 44. For illustration purposes only (this configuration would never be used knowingly during actual operation), the umbilical light transmission cable 44 is detached and withdrawn slightly from its attachment to the Y-port adapter 188 to reveal the optical fiber 98 as introduced into the branching line 156 and extending downstream within the lumen of the PD catheter 166 into the peritoneal dialysis solution region 184. As depicted, radial EMR emission is provided through the Y-site/transfer region 194, the exterior region 176 upstream of the subcutaneous cuff 172, within the tunneled region 178, and into the peritoneal dialysis solution 202 within the peritoneal dialysis region 184. This configuration demonstrates that the radial EMR emission may be supplied external to the patient's body 204 simultaneously with supplying radial EMR emission at a distinct location within the patient's body, if desired for a particular treatment need.

Figure 17:
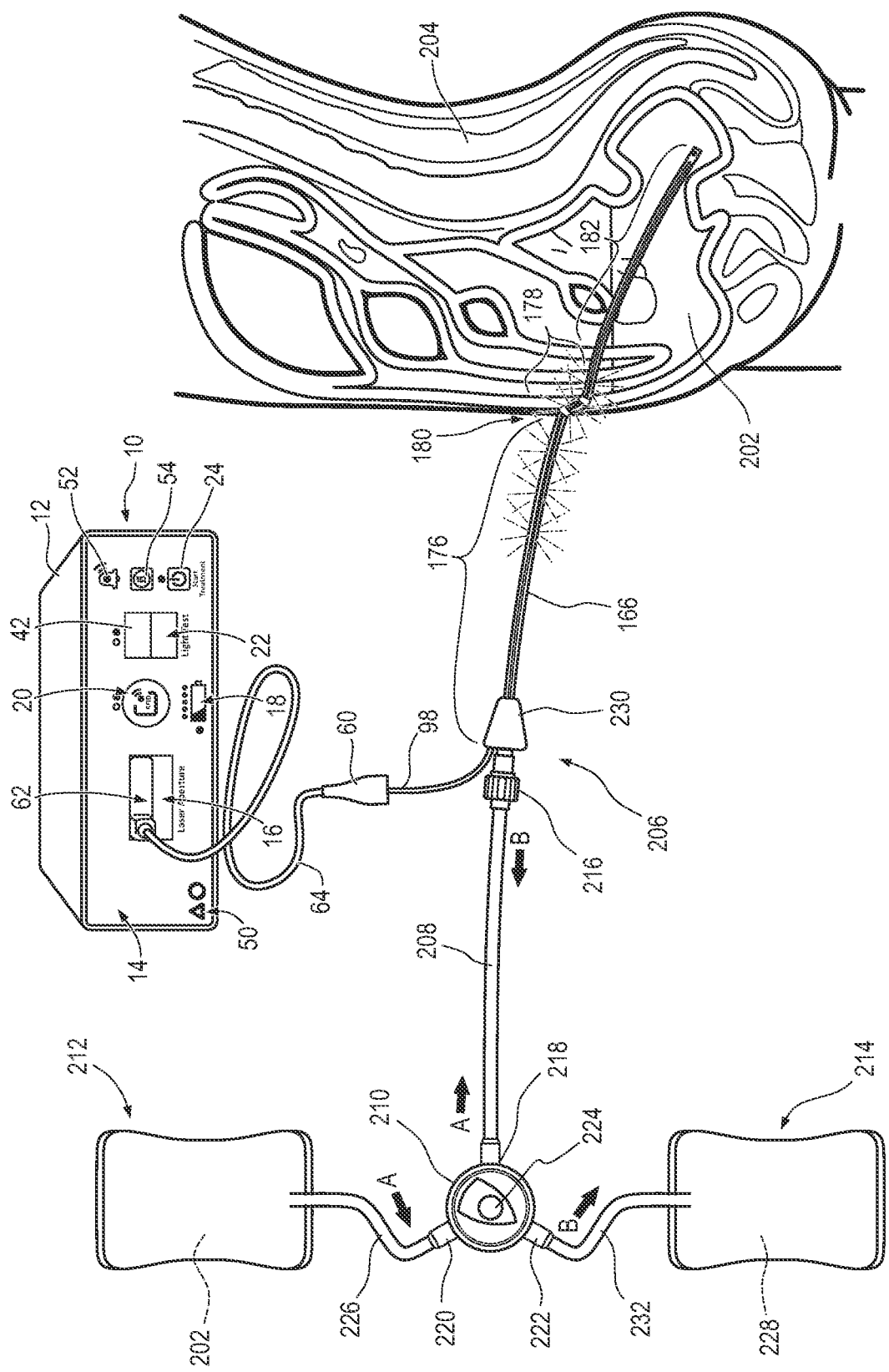
FIG. 17 is a schematic view of an exemplary embodiment of a peritoneal dialysis system showing dialysate supply and return bags and a peritoneal dialysis catheter as connected to a light engine box via an umbilical light transmission cable to supply EMIR for emission at and proximate the catheter entry site.

FIG. 17 is a schematic view of an exemplary embodiment of a peritoneal dialysis system 206 showing dialysate supply and return bags. The schematic depiction is a basic representation of peritoneal dialysis systems 206. The use of this basic representation is not intended to be limiting of the scope of the present invention; rather, this disclosure contemplates and considers the use of the disclosed invention within different or more sophisticated peritoneal dialysis systems, known and yet to be developed, to be within the scope of the present invention. For example, there are two kinds of peritoneal dialysis, Continuous Ambulatory Peritoneal Dialysis (known as CAPD) which is the kind of peritoneal dialysis depicted in FIG. 17 and Automated Peritoneal Dialysis (known as APD). CAPD is "continuous," machine-free and done while the patient goes about their normal activities. The exchange of dialysis fluids (dialysate and waste dialysate) is done manually by the user/patient and fluid flow is typically gravity driven. APD differs from CAPD in that a machine (cycler) delivers and then drains the cleansing fluid automatically for the patient. The treatment usually is done at night while the patient sleeps. Enabled by this disclosure, those skilled in the art will understand where, when, and how the delivery of EMR as disclosed herein may be used in different (such as APD systems) or more sophisticated peritoneal dialysis systems, known and yet to be developed.

The basic peritoneal dialysis system 206 (depicted in FIG. 17) comprises dialysis access via a PD catheter 166, a fluid extension line 208, a dialysate exchange switch 210, a dialysate supply bag 212, and a waste dialysate retrieval bag 214. As described with reference to FIGS. 14A-C, 15A-D, and 16A-B, the catheter (also referred to a PD catheter 166) has an external region 176, a tunneled region 178, an intra-peritoneal region 182, a coupling end and a distal end. The coupling end of the PD catheter 166 is connected to the fluid extension line 208 via an extension connector 216. The fluid extension line 208 is connected to the dialysate exchange switch 210. The dialysate exchange switch 210 has an extension line portal 218, a dialysate inlet 220, a waste dialysate outlet 222 and an exchange selector 224 for selecting fluid flow paths. The dialysate supply bag 212 contains dialysate 202 (also referred to as peritoneal dialysis solution 202) and is connected to the dialysate exchange switch 210 via a feed line 226 and the dialysate inlet 220, establishing a dialysate flow path (when the exchange selector 224 is moved to select dialysate flow) from the dialysate supply bag 212 into the feed line 226, through the dialysate exchange switch 210, into and through the fluid extension line 208, to the PD catheter 166 for delivery into the patient's body 204.

With peritoneal dialysis, a long-term, indwelling, or permanent PD catheter 166 is or may have already been inserted through the peritoneal lining into the abdominal space 184 (sometimes referred to as the peritoneal dialysis solution region 184) around the patient's organs. Dialysis solution 202 (also referred to as dialysate 202) is delivered in the direction of Arrow A from the dialysate supply bag 212 through the PD catheter 166 into that abdominal space 184. The peritoneal lining contains many blood vessels. The dialysate 202 draws extra fluid, chemicals, waste out of those blood vessels and through the peritoneal lining. Hence, the peritoneal lining acts as a filter. The dialysate 202 is left in place for a several hours while dialysis occurs. Then the old, waste-laden dialysis solution 228 (sometimes referred to as waste dialysate 228) is allowed to drain out through the PD catheter 166 for disposal. Fresh, clean solution (dialysate) 202 is immediately delivered in, filling in the abdominal space 184 again. This process of exchanging old (waste dialysate) solution 228 with new dialysate 202 is called an exchange.

The peritoneal dialysis system 206 has been enhanced by adding a light engine system 10 comprising a light engine box 12 and an optical fiber 98. This enhancement of the peritoneal dialysis system 206 may be part of a kit that includes the peritoneal dialysis system 206 and the light engine system 10 (whether the light engine system 10 is permanently connected to the peritoneal dialysis system 206 or removably insertable into the peritoneal dialysis system 206). Alternatively, the light engine system 10 may be retrofitted with an existing peritoneal dialysis system 206. As depicted, the optical fiber 98 of the light engine system 10 is introduced into the external region 176 of the PD catheter 166 through an introducing adapter 230 that facilitates the passage of the optical fiber 98 into the lumen of the PD catheter 166 without impairing the free flow of fluid through the PD catheter 166.

For illustration purposes only (this configuration would never be used knowingly during actual operation), the umbilical light transmission cable 44 is detached and withdrawn slightly from its attachment to the introducing adapter 230 to reveal the optical fiber 98 as introduced into the lumen of the PD catheter 166. When the umbilical light transmission cable 44 is connected to the light engine box 12 and the optical fiber 98 is disposed within the lumen of the PD catheter 166 (the connection between the umbilical light transmission cable 44 and the optical fiber 98 has been omitted so not to obscure other features depicted), the therapeutic, non-ultraviolet EMR may be delivered where desired. The depiction in FIG. 17 shows radial delivery of EMR within the external region 176 and the tunneled region 178 of the PD catheter 166.

Of course, it should be understood the invention of this disclosure as described herein may provide radial emission of the EMR light in the locations, at the intensities, and with the controlled relative intensity and/or treatment region specific application of therapeutic doses of the EMR light discussed above.

As depicted in FIG. 17, the dialysate exchange switch 210 is set for the waste cycle where waste dialysate 228 is withdrawn from the abdominal space 184 in the direction of Arrows B, through a dialysis access such as the PD catheter 166 and the extension connector 216, into the fluid extension line 208, into the dialysate exchange switch 210 via the extension line portal 218, and out through the waste dialysate outlet 222 into a drainage line 232 and then the waste dialysate retrieval bag 214 for disposal.

Figure 18:
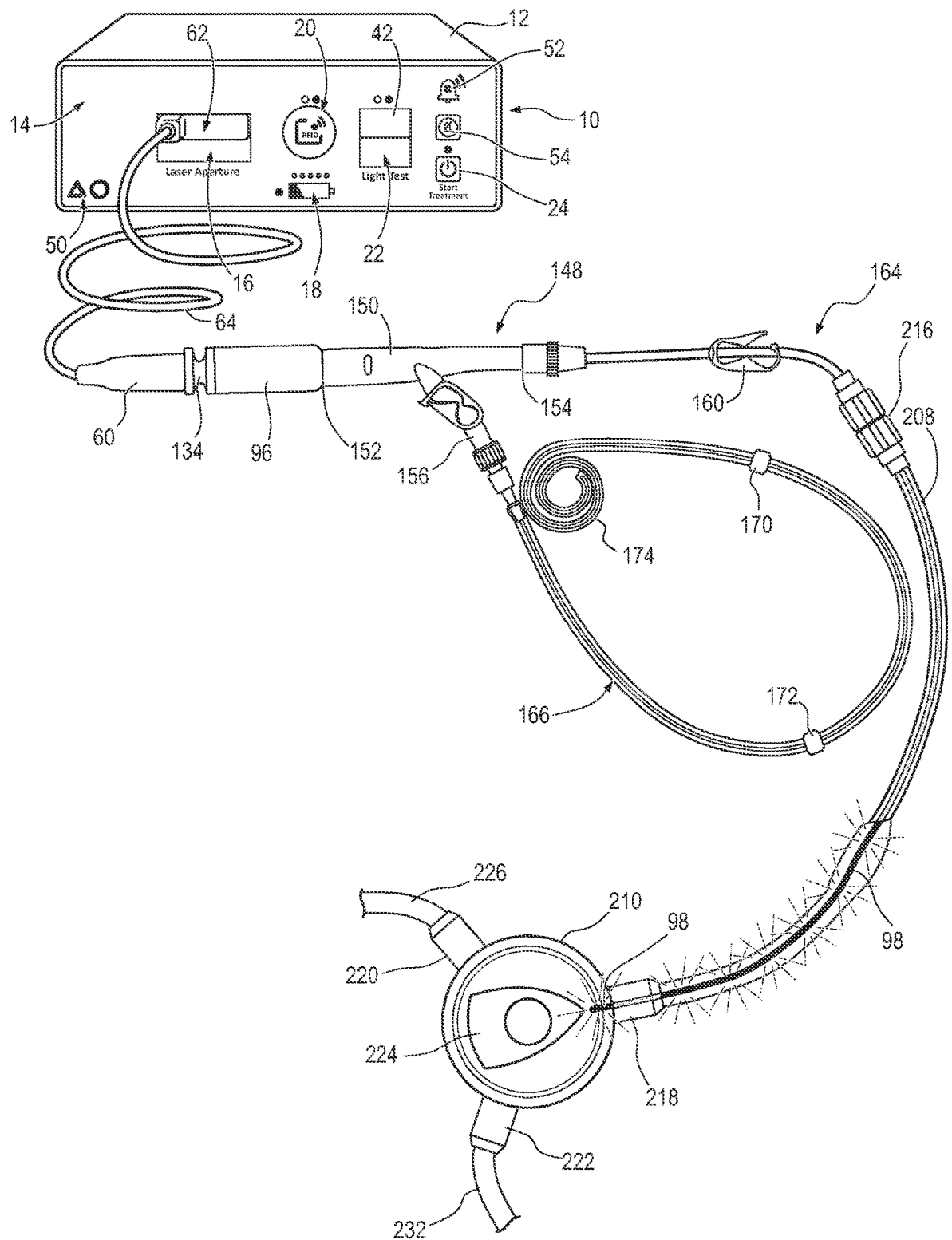
FIG. 18 is a schematic view of a portion of an exemplary embodiment of a peritoneal dialysis system showing the emission of EMR at a treatment location in a PD extension catheter and into a dialysate exchange switch.

FIG. 18 is a schematic depiction of another exemplary embodiment of a portion of the peritoneal dialysis system 206 (omitting the dialysate supply bag 212 and the waste dialysate retrieval bag 214 showing the emission of EMR light at a treatment location within the fluid extension line 208 (sometimes called a PD extension catheter) and into the dialysate exchange switch 210 in the vicinity of the extension line portal 218. This exemplary embodiment utilizes the light engine system 10 with light engine box 12, umbilical light transmission cable 44, fiber optic disposable 96, fiber optic introducer 148 for delivering EMR to the fluid extension line 208 and the dialysate exchange switch 210, where the PD catheter 166 having a coiled Tenckhoff 174 is also connected to the fiber optic introducer 148 via branching line 156. This depiction illustrates the versatility of the light engine system 10 in that it may also be used to sterilize the fluid extension line 208 and the dialysate exchange switch 210 independent of delivering EMR to the PD catheter 166 by inserting the optical fiber 98 into the fluid extension line 208. With this configuration, the therapeutic EMR may be delivered before dialysis begins, during dialysis, during waste dialysate 228 retrieval, and/or after the dialysis treatment is complete.

Figure 19:
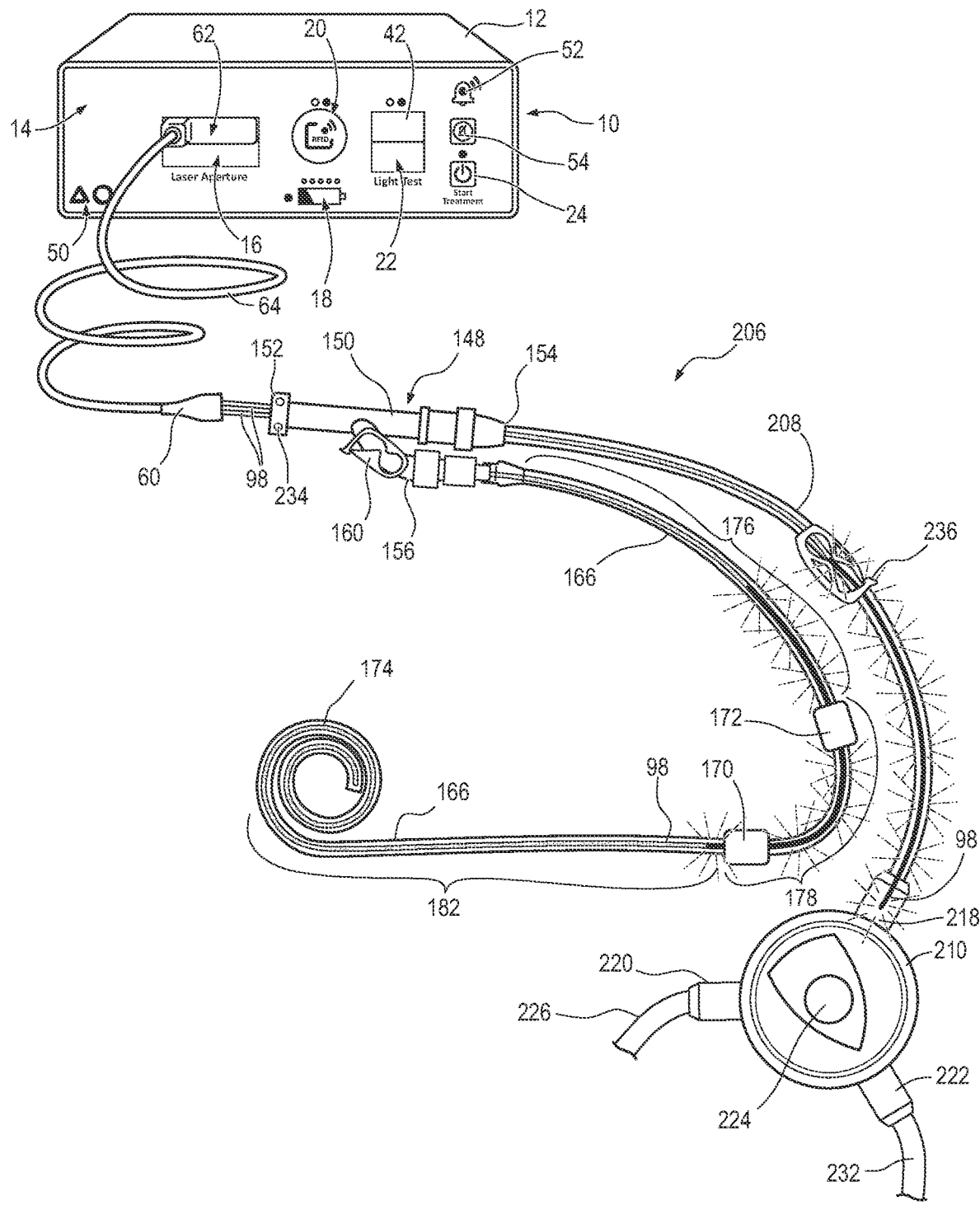
FIG. 19 is a schematic view a portion of another exemplary embodiment of a peritoneal dialysis system depicting dual EMR delivery.

FIG. 19 is a schematic depiction of another exemplary embodiment of a portion of the peritoneal dialysis system 206 (omitting the dialysate supply bag 206 and the waste dialysate retrieval bag 214) showing dual EMR delivery from the light engine box 12. With this embodiment, two optical fibers 98 extend from the distal connector 60 of the umbilical light transmission cable 44 to depict schematically that two laser assemblies 34 within the light engine box 12 supply two distinct EMR sources may connect with a dual receiver adapter 234 that receives and directs the EMR into one optical fiber 98 inserted into the fluid extension line 208, and the other optical element 18 inserted into the PD catheter 166. The EMR light delivered may be the same for each optical fiber 98. In other instances, a receiver adapter 234 may be used that split a single EMR source into two separate optical fibers 98 inside the receiver adapter 234. Also, when two or more EMR sources deliver EMR respective optical fibers 98, the EMR delivered may differ for each optical fiber 98. For example, EMR may be delivered alternatively, alternatingly, or simultaneously, and with differing frequencies, intensities, and dosages to provide controlled relative intensity and/or treatment region specific application of therapeutic doses of the EMR where and when desired within the peritoneal dialysis system 206.

FIG. 19 shows an exemplary configuration conducive to simultaneous EMR delivery into the fluid extension line 208 and the PD catheter 166. Also, depicted is a line clamp 236 used to occlude the fluid extension line 208 so that fluid (waste dialysate 228, as depicted) will not drain through the fluid extension line 208 into the waste dialysate retrieval bag 214 during the dialysis process once the peritoneal dialysis solution region 184 is filled and before the waste cycle. As depicted, the portion of the fluid extension line 208 between the line clamp 236 and the dialysate exchange switch 210 is being sterilized by the EMR radially emitting from the optical fiber 98.

Figure 20:
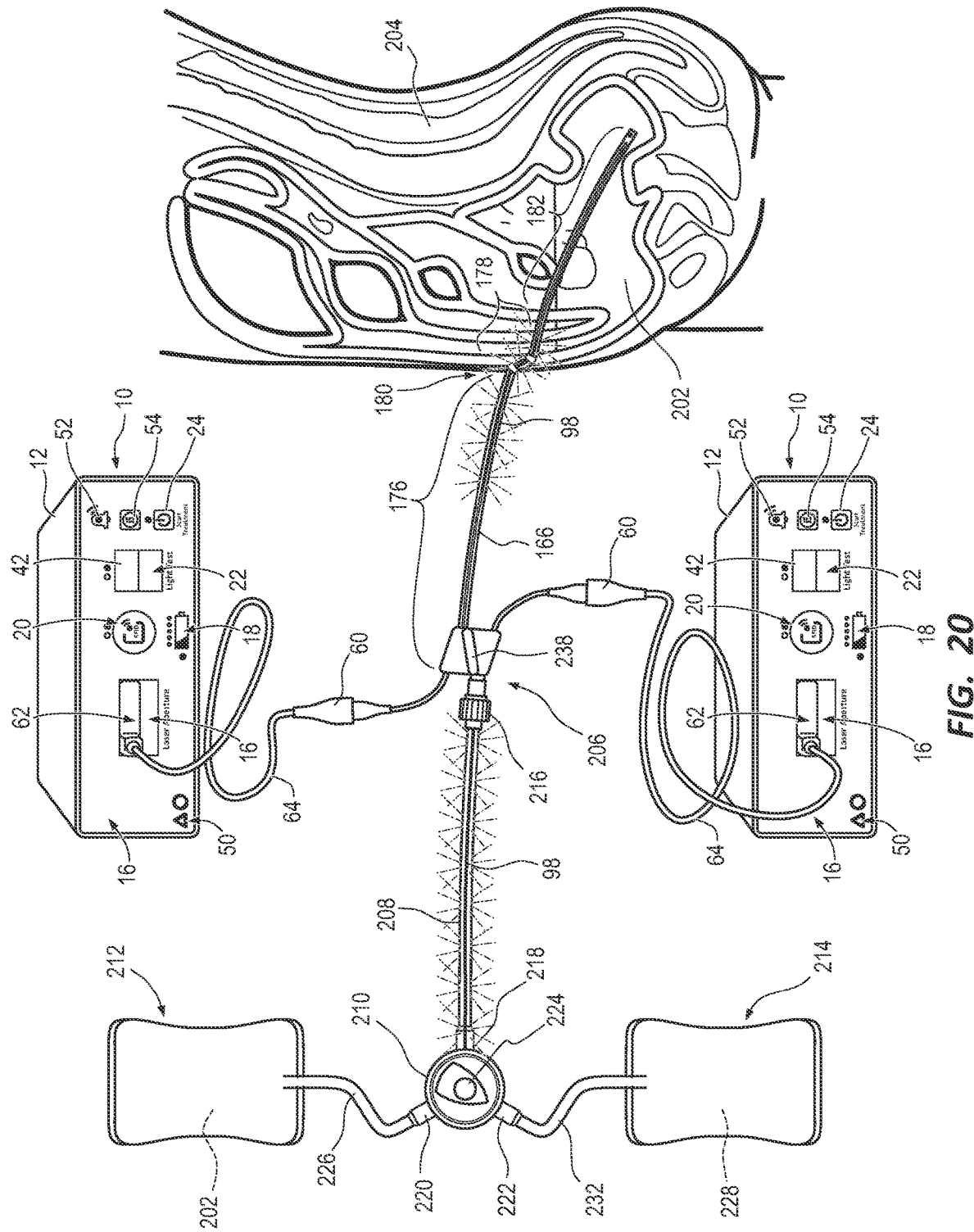
FIG. 20 is a schematic view of still another exemplary embodiment of a peritoneal dialysis system depicting another exemplary dual EMR delivery using two light engine boxes and two umbilical light transmission cables.

Still another exemplary embodiment of a peritoneal dialysis system 206 is depicted schematically in FIG. 20 showing a dual EMR delivery using two light engine systems 10. With this embodiment, two optical fibers 98 extend from separate light engine boxes 12 and into a dual introducing multi-direction adapter 238, one optical fiber 98 inserted into the fluid extension line 208, and the other optical fiber 98 inserted into the PD catheter 166. The EMR delivered may be the same for each optical fiber 98. However, separate light line boxes 12 make it possible to have each optical fiber 98 operate totally independent of the other optical fiber 98. Hence, the EMR delivered may be provided alternatively, alternatingly, or simultaneously, and with differing frequencies, intensities, and dosages so to provide controlled relative intensity and/or treatment region specific application of therapeutic doses of the EMR where and when desired within the peritoneal dialysis system 206. Specifically, FIG. 20 shows simultaneous EMR delivery into the fluid extension line 208 and the PD catheter 166; however, each may be emitting EMIR with different frequencies, intensities, and dosages.

Figure 21:
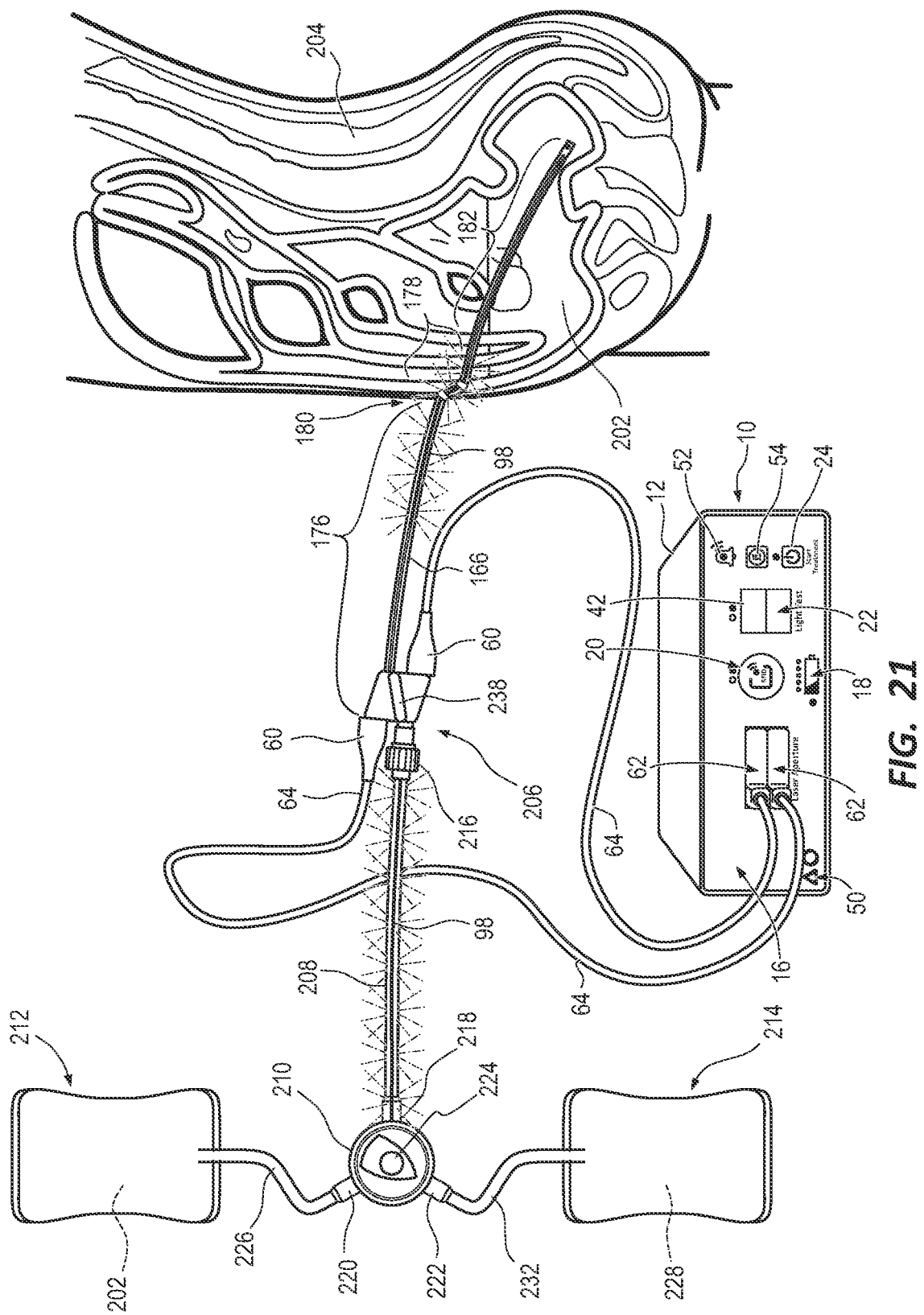
FIG. 21 is a schematic view of yet another exemplary embodiment of a peritoneal dialysis system depicting dual EMR delivery using a single light engine box with dual laser apertures.

Yet another exemplary embodiment of a peritoneal dialysis system 206 is depicted in FIG. 21 and shows dual EMR delivery (like the configuration in FIG. 20) using a single light engine box 12. With this embodiment, two umbilical light transmission cables 44 extend from the light engine box 12 (each connected to a different laser assembly 34, not shown) and each of the umbilical light transmission cables is connected to the dual introducing multi-direction adapter 238, one optical fiber 98 being inserted into the fluid extension line 208, and the other optical fiber 98 being inserted into the PD catheter 166. Again, the EMR delivered may be the same for each optical fiber 98. In this instance, however, the single light engine box 12 may deliver differing EMR to each optical fiber 98, making it possible to have each optical fiber 98 operate independent of each other. Again, the EMR delivered may be provided alternatively, alternatingly, or simultaneously, and with differing frequencies, intensities, and dosages so to provide controlled relative intensity and/or treatment region specific application of therapeutic doses of the EMR where and when desired within the peritoneal dialysis system 206. Specifically, FIG. 21 also shows simultaneous EMR delivery into the fluid extension line 208 and the PD catheter 166; however, each may be emitting EMR of different frequencies, intensities, and dosages.

Hemodialysis is a treatment that removes wastes and extra fluid from a patient's blood when the patient's own kidneys have failed. Before hemodialysis can be done, a connection must be made to the blood inside the patient's blood vessels. One of a several different types of dialysis access 240, such as a vascular access, reaches a patient's blood for hemodialysis. The dialysis access 240 allows the patient's blood to travel through soft tubes (such as extension tubing, catheters, and like tubular structures) to the dialysis machine where it is cleaned as it passes through a special filter acting as an artificial kidney, called a dialyzer. Generally, there are three principal different types of dialysis access 240 used for hemodialysis. They are called a fistula, a graft, and a catheter (or hemodialysis catheter). There are pros and cons of each one. Typically, a special surgeon with hemodialysis access experience will determine, recommend, and/or select which type of dialysis access 240 will be appropriate for each patient.

To get blood into the dialyzer, a dialysis access 240, or entrance, into the patient's blood vessels must be made. Typically, this is done with minor surgery, usually to an arm or leg or elsewhere depending on where the dialysis access 240 is most appropriate for the patient 204.

For hemodialysis, catheters are generally used as a temporary dialysis access 240, in case of an emergency need for dialysis or while waiting for dialysis access surgery to create either a fistula or a graft and for the fistula or graft to mature, but sometimes catheters provide permanent dialysis access 240. Hemodialysis catheters are soft tubes (i.e., soft tubular structures) placed into a large vein in the neck or sometimes elsewhere such as in the leg.

An arteriovenous fistula, a dialysis access 240 made by joining an artery and a vein in the patient's arm (or leg), is generally considered advantageous because it lasts longer and has fewer problems such as infections and clotting. An arteriovenous fistula should be placed several months before it is needed to start dialysis. This allows the fistula enough time to be ready for when treatment is needed and starts. A fistula usually takes one to four months to "mature" or enlarge before it can be used. However, some patients may not be able to receive a fistula because their blood vessels are not strong enough.

An arteriovenous graft is a dialysis access 240 made by joining an artery to a closely proximate vein. Minor surgery is done using an artificial tube between the vein and the nearby artery. An arteriovenous graft is usually put inside the bend of a patient's arm or in their upper arm. Sometimes, it may be placed in a patient's leg or chest wall. The arteriovenous graft generally needs to be in place at least two weeks after surgery before it can be used. Each of these dialysis access 240 options are susceptible to infectious agents.

Figure 22:
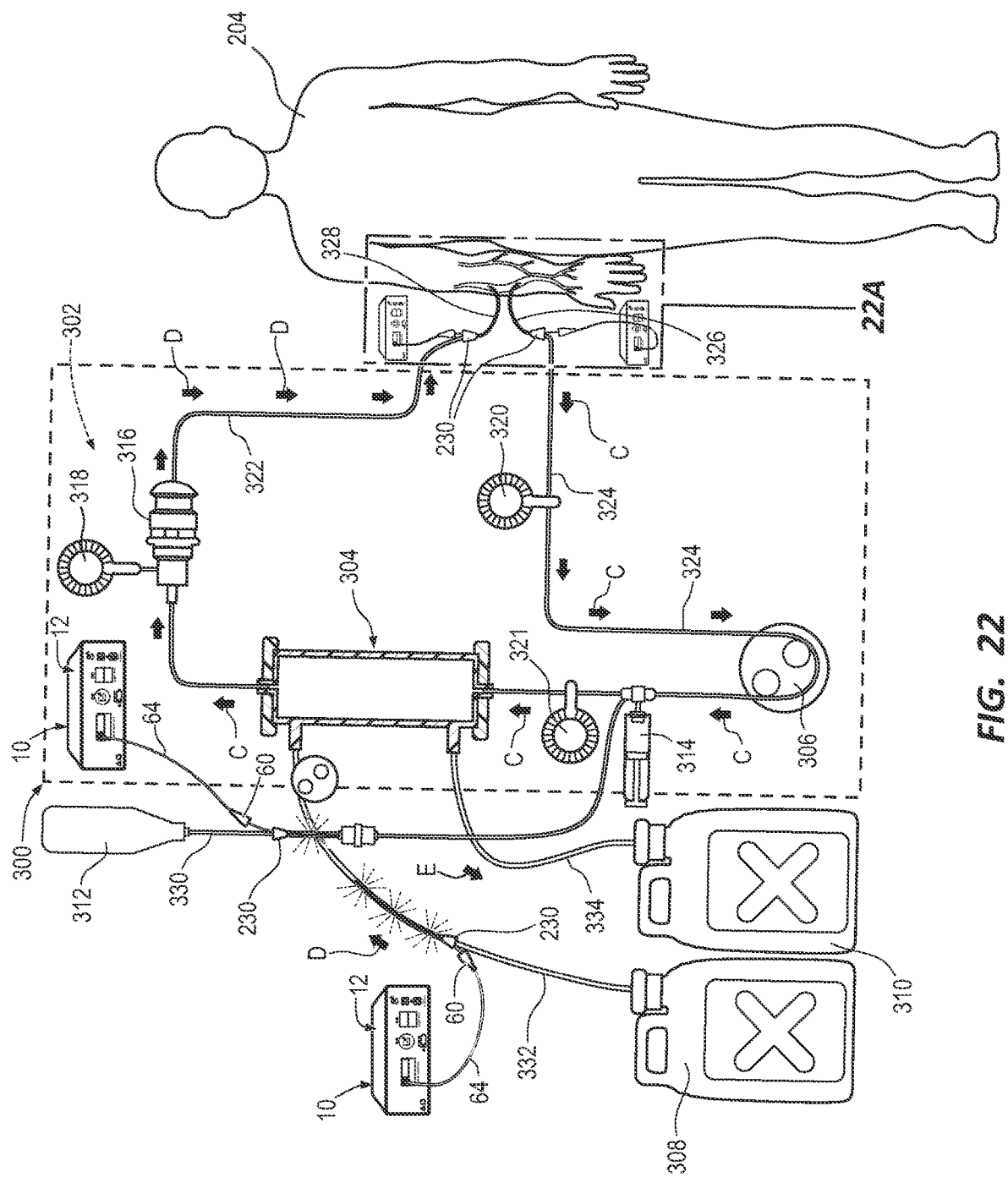
FIG. 22 is a schematic view of a representative exemplary embodiment of a hemodialysis system depicting a hemodialysis unit shown in phantom lines, components of the dialysis system pertinent to the invention of this disclosure, and an inset area enlarged as FIG. 22A.
Figure 22A:
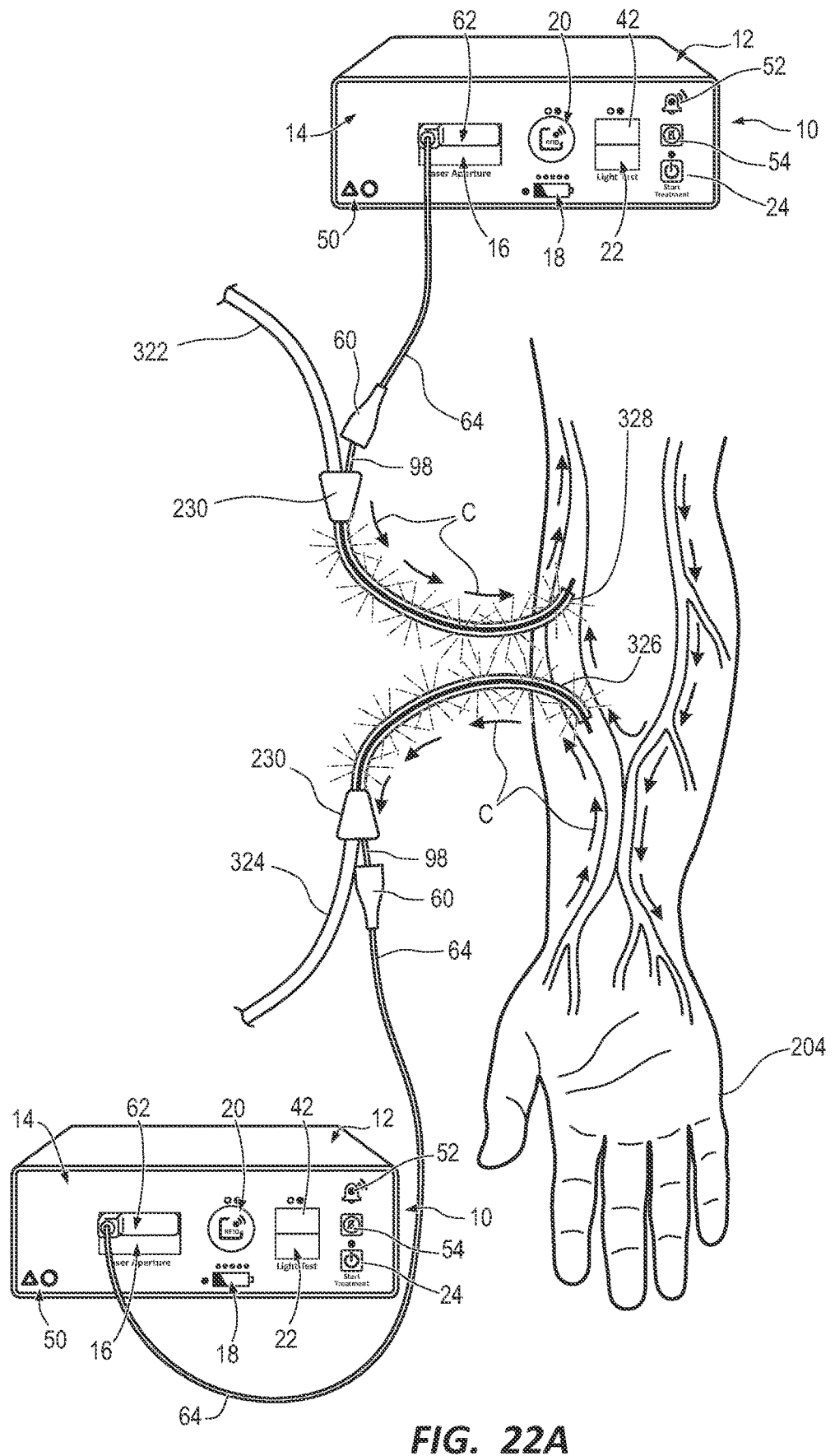
FIG. 22A is an enlargement of the inset area identified in FIG. 22 showing an exemplary dialysis access into the arm of a patient.

FIG. 22 is a schematic view of a representative exemplary embodiment of a hemodialysis system 300 depicting a hemodialysis unit 302 shown in phantom lines, components of the hemodialysis system 300 pertinent to the invention of this disclosure, and an inset area enlarged as FIG. 22A.

The components of the hemodialysis system 300 pertinent to the invention of this disclosure, include but are not limited to a dialysis access 240, a dialyzer 304, a blood pump 306, a dialysate reservoir 308, a waste dialysate reservoir 310, a saline bag 312, a heparin pump 314, an air trap/air detector 316, an arterial-pressure monitor 318, a venous-pressure monitor 320, an inflow-pressure monitor 321, an inbound blood flow tubing 322 (another exemplary tubular structure), and an outbound blood flow tubing 324 (yet another tubular structure). Some or most of these components may be enclosed within the hemodialysis unit 302. However, as depicted in FIG. 22, the dialysate reservoir 308, waste dialysate reservoir 310, and saline bag 312 are usually external to the hemodialysis unit and the dialysis access 240, being an access into the patient's body 204, is always outside the hemodialysis unit 302, FIG. 22A is an enlargement of the inset area identified in FIG. 22 showing an exemplary dialysis access 240, a representative fistula access, into the patient's 204 arm, showing an outbound venous line 326 and an inbound arterial line 328.

Blood from the patient 204 is drawn into the outbound venous line 326 and the outbound blood flow tubing 324 in the direction of Flow Arrows C, and is pumped into the dialyzer 304, where the blood is cleaned. A dialysate solution is drawn from the dialysate reservoir 308 into the dialyzer 304, in the direction of Inflow Arrow D, via a feed line 332 to interact with the venous-drawn blood, to filter it and remove waste and extra fluid from the blood, thereby serving as an artificial kidney. The cleaned, fresh blood exits the dialyzer 304 and flows (again in the direction of Flow Arrows C) into the inbound blood flow tubing 322 and then the inbound arterial line 328 to be circulated within the patient 204. The dialysate solution exiting the dialyzer 304 is waste dialysate 228 that carries out the waste, other impurities, and the extra fluid as it drains through the drainage line 334, in the direction of Drainage Arrow E, into the waste dialysate reservoir 310 for disposal.

As the filtered, fresh blood circulates through the patient's body 204, it gathers and collects waste, other impurities, and extra fluid before it again is drawn from the patient 204 into the outbound venous line 326 and the outbound blood flow tubing 324 in the direction of Flow Arrows C and is pumped into the dialyzer 304 to be cleaned. The cycle of circulation through the patient's body 204 and the hemodialysis unit 302 continues to repeat until dialysis is complete.

During dialysis, the blood pump 306 regulates the flow of the blood through the hemodialysis unit. The heparin pump 314 infuses heparin into the blood to prevent the blood from clotting. A saline solution that flows from the saline bag 312 through a saline line 330 into the outbound blood flow tubing 324 (or, in some instances, directly into the dialyzer 304) is vital to the dialysis process. It is the saline solution in the dialyzer 304 that serves as the agent used to cleanse the venous-drawn blood within the dialyzer 304. The venous-pressure monitor 320 monitors the pressure within the outbound blood flow tubing 324 so that pressure may be maintained in an operable range. Additionally, the inflow-pressure monitor 321 monitors pressure at a location downstream of the blood pump 306 and upstream of the dialyzer so that the blood entering the dialyzer is within a proper operating range for the dialyzer 304. Similarly, the arterial-pressure monitor 318 monitors the pressure within the inbound blood flow tubing 322 so that pressure may be maintained in an operable range. The air trap/air detector 316 detects and traps undesirable air bubbles within the inbound blood flow tubing 322 before such air bubbles enter the patient's body 204 and cause serious consequences to the patient 204.

During preparations for dialysis and the actual hemodialysis process, there are occasions when either the patient 204 or a person assisting the patient 204 may access or handle various connections, materials, or component parts involved in the dialysis. Such accessing or handling may introduce or increase the possibility of infectious agents contaminating the hemodialysis equipment or process. Certain components can be identified as being particularly susceptible to such contamination. Consequently, being able to sterilize such components and/or to reduce or eliminate such infectious agents could reduce or eliminate one of the most serious concerns about having to undergo dialysis.

FIG. 22 depicts several representative locations where the delivery of therapeutic EMR could be instrumental in preventing, reducing, or eliminating infections that are known to be pernicious to undergoing dialysis. Four separate light engine systems 10 are depicted in FIG. 22 as representative locations for delivering therapeutic EMR. Although each of the locations depicted are shown as external to the hemodialysis unit 302 and as such may be retrofitted into an existing hemodialysis system 300, it should be understood one or more of the light engine systems 10 may be disposed permanently within the hemodialysis unit 302. Also, although FIG. 22 depicts four separate light engine systems 10 having four separate light engine boxes 12, it should be understood one, more than one, or all EMIR delivery locations may be operated by a single light engine box 12.

As depicted, one light engine system 10 is placed to deliver EMR to sterilize the saline solution and/or the saline line 330 or inactivate infectious agents in the saline solution and/or on or in the saline line 330. This light engine system 10 comprises a light engine box 12 that provides the EMIR at the desired intensity(ies), an umbilical light transmission cable 44 that receives and conveys the EMR from the light engine box 12 through an introducing adapter 230 into the saline line 330.

Another light engine system 10 is placed to deliver EMR to sterilize the dialysate solution and/or the feed line 332 or inactivate infectious agents in the dialysate solution and/or on or in the feed line 332. This light engine system 10 comprises a light engine box 12 that provides the EMR at the desired intensity(ies), an umbilical light transmission cable 44 that receives and conveys the EMR from the light engine box 12 through an introducing adapter 230 into the feed line 332.

The other two light engine systems 10 are used to deliver EMIR to the representative dialysis access 240 are best depicted in FIG. 22A. The representative dialysis access 240 depicted is a fistula comprising an arterial access 328 and a venous access 326. The arterial access 328 and the venous access 326 comprises access needles (not shown) and the inbound blood flow tubing 322 and outbound blood flow tubing 324, respectively. One of the light engine systems 10 is placed to deliver EMIR to sterilize blood and/or the outbound blood flow tubing 324 or inactivate infectious agents in the blood and/or on or in the outbound blood flow tubing 324. The other light engine system 10 is placed to deliver EMIR to sterilize blood and/or the inbound blood flow tubing 322 or inactivate infectious agents in the blood and/or on or in the inbound blood flow tubing 322. Each light engine system 10 comprises a light engine box 12 that provides the EMR at the desired intensity(ies), an umbilical light transmission cable 44 that receives and conveys the EMR from the light engine box 12 through an introducing adapter 230 into the outbound blood flow tubing 324 and the inbound blood flow tubing 322, respectively.

For exemplary methods or processes of the invention, the sequence and/or arrangement of steps described herein are illustrative and not restrictive. Accordingly, it should be understood although steps of various processes or methods may be shown and described as being in a sequence or temporal arrangement, the steps of any such processes or methods are not limited to being carried out in any one sequence or arrangement, absent an indication otherwise. Indeed, the steps in such processes or methods generally may be carried out in various sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Exemplary embodiments of the present invention are described above. No element, act, or instruction used in this description should be construed as important, necessary, critical, or essential to the invention unless explicitly described as such. Although several exemplary embodiments have been described in detail herein, those skilled in the art will readily appreciate that many modifications are possible in these exemplary embodiments without materially departing from the novel teachings and advantages of this invention. For example, the delivery of EMR via an optical element comprising a fiber optic, as disclosed, and claimed herein, is not limited to delivery of EMIR in, on, and around catheters only, but may also deliver EMIR in, on, and around other tubular structures. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under Section 112, 6th paragraph is not intended. Additionally, it is not intended that the scope of patent protection afforded the present invention be defined by reading into any claim a limitation found herein that does not explicitly appear in the claim itself.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. An electromagnetic radiation (EMR) delivery system for delivering EMR at wavelengths, intensities, exposures, and durations to locations inside and/or outside a patient's body in, on, and surrounding a tubular structure having a lumen and comprising a tube, a catheter, and/or a catheter extension, to prevent, reduce, and/or eliminate infectious agents in, on, or surrounding the tubular structure and/or to enhance healthy cell growth, the EMR delivery system being connected to a power supply and comprising:
   at least one light engine box for connection to the power supply and for generating therapeutic EMR, each light engine box comprising:
      at least one laser assembly disposed within the light engine box that receives power from the power supply and generates a non-ultraviolet, therapeutic EMR having an intensity comprising a range of radiant exposures from 0.1 $J/cm^2$ to 5 $kJ/cm^2$, and a range of powers from 0.005 mW to 5 W, and a power density range from 1 $mW/cm^2$ and 2 $W/cm^2$, such intensity being sufficient to produce a therapeutic effect of at least one of inactivating one or more infectious agents and enhancing healthy cell growth; and
      at least one cable adapter, each cable adapter being connected to one laser assembly;
   a light transmission cable having a proximate end and a distal end, the proximate end being connected with the cable adapter, the cable adapter for receiving therapeutic EMR from the laser assembly and facilitating the propagation of the therapeutic EMR from the laser assembly to and through the light transmission cable to the distal end of the light transmission cable for delivery to the tubular structure; and
   an optical element connected to the light transmission cable, the optical element comprising a fiber optic for disposition within the lumen of the tubular structure, the fiber optic being conducive to the axial propagation of the therapeutic EMR relative to the tubular structure, the fiber optic further comprises at least one radial emission portion disposed between a coupling end of the fiber optic and a distal end of the fiber optic.

2. The EMR delivery system of claim 1 wherein the light engine box is a smart light engine box and further comprises a central processing unit (CPU) that controls features provided by the smart light engine box, the CPU being connected to the power supply and being at least one of pre-programmed and programmable.

3. The EMR delivery system of claim 2 wherein the smart light engine box further comprises a test module and a subminiature version A (SMA) optical fiber connector, the SMA optical fiber connector facilitates the connection of the test module to the distal end of the light transmission cable such that therapeutic EMR is delivered to the test module from the distal end of the light transmission cable and the delivered therapeutic EMR is tested by the test module, the test module sends test results to the CPU to be analyzed against predetermined EMR parameters and the CPU determines the health of the laser assembly and any degradation in the therapeutic EMR delivered to the test module.

4. The EMR delivery system of claim 3 wherein the smart light engine box further comprises an alarm alert that activates when the CPU indicates to the alarm alert that the therapeutic EMR fails to meet the predetermined therapeutic EMR parameters, indicating that one of the health of the laser assembly is compromised or the light transmission cable has degraded and requires replacement.

5. The EMR delivery system of claim 2 wherein the smart light engine box further comprises a treatment actuator to initiate a pre-programmed dosing treatment of therapeutic EMR meeting the predetermined therapeutic EMR parameters, the treatment actuator being manually activated.

6. The EMR delivery system of claim 5 wherein the smart light engine box further comprises an alarm alert that activates when the CPU indicates to the alarm alert that the smart light engine box is in a failure mode, the treatment actuator being manually deactivated when the failure mode is indicated.

7. The EMR delivery system of claim 2 wherein the light transmission cable is an umbilical light transmission cable comprising at least one transmission wire to facilitate the transmission of at least one of data and electricity.

8. The EMR delivery system of claim 7 wherein the smart light engine box further comprises an alarm alert that activates when the CPU indicates to the alarm alert that any transmission within any transmission wire has been disrupted.

9. The EMR delivery system of claim 2 wherein the optical element comprises a fiber optic disposable, the fiber optic disposable has an elongate structure, a retracted mode, and a fiber-advanced mode and comprises the fiber optic, a proximal end for connection to the distal end of the light transmission cable, a distal end for advancing into the tubular structure, the fiber optic is maintained in a sterile environment when the fiber optic disposable is in the retracted mode, when the fiber optic is advanced into the lumen of the tubular structure the fiber optic disposable is in the fiber-advanced mode.

10. The EMR delivery system of claim 9 wherein the fiber optic further comprises at least one radial emission portion disposed between the proximal end of the fiber optic and the distal end of the fiber optic.

11. An EMR delivery system for delivering EMR at wavelengths, intensities, exposures, and durations to locations inside and/or outside a patient's body in, on, and surrounding a tubular structure having a lumen and comprising a tube, a catheter, and/or a catheter extension, to prevent, reduce, and/or eliminate infectious agents in, on, or surrounding the tubular structure and/or to enhance healthy cell growth, the EMR delivery system being connected to a power supply and comprising:
   a CPU that controls features provided by the smart light engine box, the CPU being connected to the power supply and being at least one of pre-programmed and programmable,
   at least one smart light engine box for connection to the power supply and for generating therapeutic EMR, each smart light engine box comprising:
      at least one laser assembly disposed within the light engine box that receives power from the power supply and generates a non-ultraviolet, therapeutic EMR having an intensity comprising a range of radiant exposures from 0.1 $J/cm^2$ to 5 $kJ/cm^2$, and a range of powers from 0.005 mW to 5 W, and a power density range from 1 $mW/cm^2$ and 2 $W/cm^2$, such intensity being sufficient to produce a therapeutic effect of at least one of inactivating one or more infectious agents and enhancing healthy cell growth; and at least one cable adapter, each cable adapter being connected to one laser assembly via an SMA optical fiber connector;

an umbilical light transmission cable having a proximate end and a distal end, the proximate end being connected with the cable adapter, the cable adapter for receiving therapeutic EMR from the laser assembly and facilitating the propagation of the therapeutic EMR from the laser assembly to and through the umbilical light transmission cable to the distal end of the umbilical light transmission cable for delivery to the tubular structure, the umbilical light transmission cable comprising at least one transmission wire to facilitate the transmission of at least one of data and electricity; and a fiber optic disposable, the fiber optic disposable having an elongate structure, a retracted mode, and a fiber-advanced mode and comprises a fiber optic, a proximal end for connection with the distal end of the umbilical light transmission cable, a distal end for advancing into the lumen of the tubular structure, the fiber optic is maintained in a sterile environment when the fiber optic disposable is in the retracted mode, when the fiber optic is advanced into the lumen of the tubular structure the fiber optic disposable is in the fiber-advanced mode, the fiber optic being conducive to the axial propagation of the therapeutic EMR relative to the tubular structure when in the fiber-advanced mode, the fiber optic further comprises at least one radial emission portion disposed between proximal end of the fiber optic and a distal end of the fiber optic.

12. The EMR delivery system of claim 11 wherein the CPU blocks actuation of the laser assembly when the monitoring of usage of the fiber optic disposable is unable to complete another treatment before the predetermined useful life of the fiber optic disposable is exhausted.

13. The EMR delivery system of claim 11 wherein the smart light engine box further comprises a treatment actuator to initiate a pre-programmed dosing treatment of therapeutic EMR meeting the predetermined therapeutic EMR parameters, the treatment actuator being manually activated.

14. The EMR delivery system of claim 13 wherein the smart light engine box further comprises an alarm alert that activates when the CPU indicates to the alarm alert that the smart light engine box is in a failure mode, the treatment actuator being manually deactivated when the failure mode is indicated.

15. An EMR delivery fiber optic disposable for delivering EMR at wavelengths, intensities, exposures, and durations to locations inside and/or outside a patient's body in, on, and surrounding a tubular structure having a lumen to prevent, reduce, and/or eliminate infectious agents in, on, or surrounding the tubular structure, the EMR delivery fiber optic disposable being connected to an EMR delivery system connected to a power supply, the EMR delivery system comprising a CPU that controls features of the EMR delivery system, at least one laser assembly that receives power from the power supply and generates a non-ultraviolet, therapeutic EMR having an intensity sufficient to produce a therapeutic effect of at least one of inactivating one or more infectious agents and enhancing healthy cell growth, a light transmission cable having a proximate end and a distal end, the proximate end being connected the laser assembly for receiving therapeutic EMR from the laser assembly and facilitating the propagation of the therapeutic EMR from the laser assembly to and through the light transmission cable to the distal end of the light transmission cable, the EMR delivery fiber optic disposable comprising:

a fiber optic disposable, the fiber optic disposable having an elongate structure, a retracted mode, and a fiber-advanced mode and comprises a fiber optic, a proximal end for connection to the distal end of the light transmission cable, a distal end for advancing into the lumen of the tubular structure, the fiber optic is maintained in a sterile environment when the fiber optic disposable is in the retracted mode, when the fiber optic is advanced into the lumen of the tubular structure the fiber optic disposable is in the fiber-advanced mode, the fiber optic being conducive to the axial propagation of the therapeutic EMR relative to the tubular structure, the fiber optic further comprises at least one radial emission portion disposed between the proximal end of the fiber optic and a distal end of the fiber optic.

16. The EMR delivery fiber optic disposable of claim 15 wherein the EMR delivery system further comprises a fiber optic introducer for disposition intermediate of the fiber optic disposable and the tubular structure, the fiber optic introducer comprising a main line, an entry port, an exit port, a branching line, and a side port.

17. The EMR delivery fiber optic disposable of claim 16 wherein the main line is tubular and has the entry port and the exit port disposed at opposite ends of the mainline and the branching line communicates with the main line and has the side port forming a Y-connector, the entry port is connected to the distal end of the fiber optic disposable, the exit port is connected to the tubular structure, the side port is connected to a second tubular structure, the fiber optic passes through the entry port into the main line and through the exit port into the tubular structure when the fiber optic disposable is in the fiber-advanced mode, fluid flows through the exit port, the main line, the branching line, the side port, into and out of the second tubular structure.

18. The EMR delivery fiber optic disposable of claim 17 wherein the fiber optic has at least one radial emission portion disposed within the main line.

19. The EMR delivery fiber optic disposable of claim 17 wherein the fiber optic has at least one radial emission portion disposed within the tubular structure.

20. The EMR delivery fiber optic disposable of claim 16 wherein the main line is tubular and has the entry port and the exit port disposed at opposite ends of the mainline and the branching line communicates with the main line and has the side port forming a Y-connector, the entry port is connected to the distal end of the fiber optic disposable, the exit port is connected to the tubular structure, the side port is connected to a second tubular structure, the fiber optic passes through the entry port into the main line and through the branching line and side port into the second tubular structure when the fiber optic disposable is in the fiber-advanced mode, fluid dialysate flows through the exit port, the main line, the branching line, the side port, into and out of the second tubular structure.

* * * * *